(12) United States Patent
Nonaka et al.

(10) Patent No.: US 8,293,506 B2
(45) Date of Patent: Oct. 23, 2012

(54) L-CYSTEINE-PRODUCING BACTERIUM AND A METHOD FOR PRODUCING L-CYSTEINE

(75) Inventors: Gen Nonaka, Kawasaki (JP); Hiroshi Takagi, Ikoma (JP); Iwao Ohtsu, Ikoma (JP); Natthawut Wiriyathanawudhiwong, Ikoma (JP); Takeshi Nakatani, Ikoma (JP)

(73) Assignee: Ajinomoto Co., Inc., Tokyo (JP)

( * ) Notice: Subject to any disclaimer, the term of this patent is extended or adjusted under 35 U.S.C. 154(b) by 268 days.

(21) Appl. No.: 12/711,299

(22) Filed: Feb. 24, 2010

(65) Prior Publication Data

US 2010/0216196 A1 Aug. 26, 2010

Related U.S. Application Data

(60) Provisional application No. 61/155,513, filed on Feb. 25, 2009.

(30) Foreign Application Priority Data

Feb. 25, 2009 (JP) ................................ 2009-042561

(51) Int. Cl.
*C12P 13/12* (2006.01)
*C12N 1/20* (2006.01)
(52) U.S. Cl. ................ 435/113; 435/252.3; 435/252.33
(58) Field of Classification Search .................. 435/113, 435/252.3, 252.33
See application file for complete search history.

(56) References Cited

U.S. PATENT DOCUMENTS

| 5,972,663 | A | 10/1999 | Winterhalter et al. |
| 6,218,168 | B1 | 4/2001 | Leinfelder et al. |
| 6,673,569 | B1 | 1/2004 | Kurokawa et al. |
| 7,312,058 | B2 | 12/2007 | Kashiwagi et al. |
| 2003/0077766 | A1 | 4/2003 | Takagi et al. |
| 2005/0112731 | A1 | 5/2005 | Kashiwagi et al. |
| 2005/0221453 | A1 | 10/2005 | Takagi et al. |
| 2008/0076163 | A1 | 3/2008 | Takagi et al. |
| 2009/0226983 | A1 | 9/2009 | Nonaka et al. |
| 2009/0226984 | A1 | 9/2009 | Nonaka et al. |
| 2010/0093045 | A1 | 4/2010 | Takagi et al. |

FOREIGN PATENT DOCUMENTS

| CA | 2 386 539 | 4/2001 |
| JP | 05-336986 | 12/1993 |
| JP | 11-155571 | 6/1999 |
| JP | 2000-083670 | 3/2000 |
| JP | 2002-233384 | 8/2002 |
| JP | 2003-169668 | 6/2003 |
| JP | 2005-245311 | 9/2005 |
| JP | 2005-287333 | 10/2005 |
| WO | WO01/27307 | 4/2001 |

OTHER PUBLICATIONS

Kadokura, H., et al., "Snapshots of DsbA in Action: Detection of Proteins in the Process of Oxidative Folding," Science 2004;303:534-537.
Akiyama, Y., et al., "In Vitro Catalysis of Oxidative Folding of Disulfide-bonded Proteins by the *Escherichia coli* dsbA (*ppfA*) Gene Product," J. Biol. Chem. 1992;267(31):22440-22445.
Andersen, C. L., et al., "A new *Escherichia coli* gene, *dsbG*, encodes a periplasmic protein involved in disulphide bond formation, required for recycling DsbA/DsbB and DsbC redox proteins," Mol. Microbiol. 1997;26(1):121-132.
Bardwell, J. C. A., et al., "Identification of a Protein Required for Disulfide Bond Formation In Vivo," Cell 1991;67:581-589.
Bardwell, J. C. A., "Building bridges: disulphide bond formation in the cell," Mol. Microbiol. 1994:14(2):199-205.
Daβler, T., et al., "Identification of a major facilitator protein from *Escherichia coli* involved in efflux of metabolites of the cysteine pathway," Mol. Microbiol. 2000;36(5):1101-1112.
Givol, D., et al., "Oxidation and Disulfide Interchange in the Reactivation of Reduced Ribonuclease," J. Biol. Chem. 1964;239(9):3114-3116.
Inaba, K., et al., "DsbB Elicits a Red-shift of Bound Ubiquinone during the Catalysis of DsbA Oxidation," J. Biol. Chem. 2004;279(8):6761-6768.
Kadokura, H., et al., "Mutational Alterations of the Key cis Proline Residue That Cause Accumulation of Enzymatic Reaction Intermediates of DsbA, a Member of the Thioredoxin Superfamily," J. Bacteriol. 2005;187(4):1519-1522.
Missiakas, D., et al., "Identification and characterization of a new disulfide isomerase-like protein (DsbD) in *Escherichia coli*," The EMBO Journal 1995;14(14):3415-3424.
Rietsch, A., et al., "An in vivo pathway for disulfide bond isomerization in *Escherichia coil*," Proc. Natl. Acad. Sci. USA 1996;93:13048-13053.
Rietsch, A., et al., "Reduction of the Periplasmic Disulfide Bond Isomerase, DsbC, Occurs by Passage of Electrons from Cytoplasmic Thioredoxin," J. Bacteriol. 1997;179(21):6602-6608.
Shevchik, V. E., et al., "Characterization of DsbC, a periplasmic protein of *Erwinia chrysanthemi* and *Escherichia coil* with disulfide isomerase activity," The EMBO Journal 1994;13(8):2007-2012.
Sone, M., et al., "Differential in Vivo Roles Played by DsbA and DsbC in the Formation of Protein Disulfide Bonds," J. Biol. Chem. 1997;272(16):10349-10352.

*Primary Examiner* — Tekchand Saidha
(74) *Attorney, Agent, or Firm* — Shelly Guest Cermak; Cermak Nakajima LLP

(57) ABSTRACT

The present invention provides a bacterium belonging to the family Enterobacteriaceae, which is able to produce L-cysteine and has been modified to increase the activity of the protein encoded by the dsbA gene. This bacterium is cultured in a medium, and L-cysteine, L-cystine, a derivative or precursor thereof or a mixture thereof can be collected from the medium.

11 Claims, 4 Drawing Sheets

SEQUENCE LISTING

```
<160> NUMBER OF SEQ ID NOS: 14

<210> SEQ ID NO 1
<211> LENGTH: 627
<212> TYPE: DNA
<213> ORGANISM: Escherichia coli
<220> FEATURE:
<221> NAME/KEY: CDS
<222> LOCATION: (1)..(627)

<400> SEQUENCE: 1 atg aaa aag att tgg ctg gcg ctg gct ggt tta gtt tta gcg ttt agc      48
Met Lys Lys Ile Trp Leu Ala Leu Ala Gly Leu Val Leu Ala Phe Ser
1               5                   10                  15 gca tcg gcg gcg cag tat gaa gat ggt aaa cag tac act acc ctg gaa      96
Ala Ser Ala Ala Gln Tyr Glu Asp Gly Lys Gln Tyr Thr Thr Leu Glu
            20                  25                  30 aaa ccg gta gct ggc gcg ccg caa gtg ctg gag ttt ttc tct ttc ttc     144
Lys Pro Val Ala Gly Ala Pro Gln Val Leu Glu Phe Phe Ser Phe Phe
        35                  40                  45
```

```
tgc ccg cac tgc tat cag ttt gaa gaa gtt ctg cat att tct gat aat    192
Cys Pro His Cys Tyr Gln Phe Glu Glu Val Leu His Ile Ser Asp Asn
 50                  55                  60 gtg aag aaa aaa ctg ccg gaa ggc gtg aag atg act aaa tac cac gtc    240
Val Lys Lys Lys Leu Pro Glu Gly Val Lys Met Thr Lys Tyr His Val
 65                  70                  75                  80 aac ttc atg ggt ggt gac ctg ggc aaa gat ctg act cag gca tgg gct    288
Asn Phe Met Gly Gly Asp Leu Gly Lys Asp Leu Thr Gln Ala Trp Ala
                 85                  90                  95 gtg gcg atg gcg ctg ggc gtg gaa gac aaa gtg act gtt ccg ctg ttt    336
Val Ala Met Ala Leu Gly Val Glu Asp Lys Val Thr Val Pro Leu Phe
            100                 105                 110 gaa ggc gta cag aaa acc cag acc att cgt tct gct tct gat atc cgc    384
Glu Gly Val Gln Lys Thr Gln Thr Ile Arg Ser Ala Ser Asp Ile Arg
            115                 120                 125 gat gta ttt atc aac gca ggt att aaa ggt gaa gag tac gac gcg gcg    432
Asp Val Phe Ile Asn Ala Gly Ile Lys Gly Glu Glu Tyr Asp Ala Ala
130                 135                 140 tgg aac agc ttc gtg gtg aaa tct ctg gtc gct cag cag gaa aaa gct    480
Trp Asn Ser Phe Val Val Lys Ser Leu Val Ala Gln Gln Glu Lys Ala
145                 150                 155                 160 gca gct gac gtg caa ttg cgt ggc gtt ccg gcg atg ttt gtt aac ggt    528
Ala Ala Asp Val Gln Leu Arg Gly Val Pro Ala Met Phe Val Asn Gly
                165                 170                 175 aaa tat cag ctg aat ccg cag ggt atg gat acc agc aat atg gat gtt    576
Lys Tyr Gln Leu Asn Pro Gln Gly Met Asp Thr Ser Asn Met Asp Val
                180                 185                 190 ttt gtt cag cag tat gct gat aca gtg aaa tat ctg tcc gag aaa aaa    624
Phe Val Gln Gln Tyr Ala Asp Thr Val Lys Tyr Leu Ser Glu Lys Lys
            195                 200                 205 taa                                                                627
```

<210> SEQ ID NO 2
<211> LENGTH: 208
<212> TYPE: PRT
<213> ORGANISM: Escherichia coli

<400> SEQUENCE: 2

```
Met Lys Lys Ile Trp Leu Ala Leu Ala Gly Leu Val Leu Ala Phe Ser
 1               5                  10                  15

Ala Ser Ala Ala Gln Tyr Glu Asp Gly Lys Gln Tyr Thr Thr Leu Glu
                20                  25                  30

Lys Pro Val Ala Gly Ala Pro Gln Val Leu Glu Phe Phe Ser Phe Phe
            35                  40                  45

Cys Pro His Cys Tyr Gln Phe Glu Glu Val Leu His Ile Ser Asp Asn
 50                  55                  60

Val Lys Lys Lys Leu Pro Glu Gly Val Lys Met Thr Lys Tyr His Val
 65                  70                  75                  80

Asn Phe Met Gly Gly Asp Leu Gly Lys Asp Leu Thr Gln Ala Trp Ala
                 85                  90                  95

Val Ala Met Ala Leu Gly Val Glu Asp Lys Val Thr Val Pro Leu Phe
            100                 105                 110

Glu Gly Val Gln Lys Thr Gln Thr Ile Arg Ser Ala Ser Asp Ile Arg
            115                 120                 125

Asp Val Phe Ile Asn Ala Gly Ile Lys Gly Glu Glu Tyr Asp Ala Ala
130                 135                 140

Trp Asn Ser Phe Val Val Lys Ser Leu Val Ala Gln Gln Glu Lys Ala
145                 150                 155                 160
```

```
Ala Ala Asp Val Gln Leu Arg Gly Val Pro Ala Met Phe Val Asn Gly
            165                 170                 175

Lys Tyr Gln Leu Asn Pro Gln Gly Met Asp Thr Ser Asn Met Asp Val
        180                 185                 190

Phe Val Gln Gln Tyr Ala Asp Thr Val Lys Tyr Leu Ser Glu Lys Lys
        195                 200                 205

<210> SEQ ID NO 3
<211> LENGTH: 627
<212> TYPE: DNA
<213> ORGANISM: Shigella flexneri
<220> FEATURE:
<221> NAME/KEY: CDS
<222> LOCATION: (1)..(627)

<400> SEQUENCE: 3 atg aaa aag att tgg ctg gcg ctg gct ggt tta gtt tta gcg ttt agc      48
Met Lys Lys Ile Trp Leu Ala Leu Ala Gly Leu Val Leu Ala Phe Ser
1               5                   10                  15 gca tcg gcg gcg cag tat gaa gat ggt aaa cag tac act acc ctg gaa      96
Ala Ser Ala Ala Gln Tyr Glu Asp Gly Lys Gln Tyr Thr Thr Leu Glu
                20                  25                  30 aaa ccg gta gct ggc gcg ccg caa gtg ctg gag ttt ttc tct ttc ttc     144
Lys Pro Val Ala Gly Ala Pro Gln Val Leu Glu Phe Phe Ser Phe Phe
            35                  40                  45 tgc ccg cac tgc tat cag ttt gaa gaa gtt ctg cat att tct gat aat     192
Cys Pro His Cys Tyr Gln Phe Glu Glu Val Leu His Ile Ser Asp Asn
        50                  55                  60 gtg aag aaa aaa ctg ccg gaa ggc gtg aag atg act aaa tac cac gtc     240
Val Lys Lys Lys Leu Pro Glu Gly Val Lys Met Thr Lys Tyr His Val
65                  70                  75                  80 aac ttc atg ggt ggt gac ctg ggc aaa gat ctg act cag gca tgg gct     288
Asn Phe Met Gly Gly Asp Leu Gly Lys Asp Leu Thr Gln Ala Trp Ala
                85                  90                  95 gtg gcg atg gcg ctg ggc gtg gaa gac aaa gtg act gtt ccg ctg ttt     336
Val Ala Met Ala Leu Gly Val Glu Asp Lys Val Thr Val Pro Leu Phe
            100                 105                 110 gaa ggc gta cag aaa acc cag acc att cgt tca gca tct gat atc cgc     384
Glu Gly Val Gln Lys Thr Gln Thr Ile Arg Ser Ala Ser Asp Ile Arg
        115                 120                 125 gat gta ttt atc aat gca ggt att aaa ggt gaa gag tac gac gcg gcg     432
Asp Val Phe Ile Asn Ala Gly Ile Lys Gly Glu Glu Tyr Asp Ala Ala
    130                 135                 140 tgg aac agc ttc gtg gtg aaa tct ctg gtc gct cag cag gaa aaa gcc     480
Trp Asn Ser Phe Val Val Lys Ser Leu Val Ala Gln Gln Glu Lys Ala
145                 150                 155                 160 gca gct gat gtg caa ttg cgt ggt gtt ccg gcg atg ttt gtt aac ggt     528
Ala Ala Asp Val Gln Leu Arg Gly Val Pro Ala Met Phe Val Asn Gly
                165                 170                 175 aaa tat cag ctg aat ccg cag ggt atg gat acc agc aat atg gat gtt     576
Lys Tyr Gln Leu Asn Pro Gln Gly Met Asp Thr Ser Asn Met Asp Val
            180                 185                 190 ttt gtt cag cag tat gct gat acg gtg aaa tat ctg tcc gag gaa aaa     624
Phe Val Gln Gln Tyr Ala Asp Thr Val Lys Tyr Leu Ser Glu Glu Lys
        195                 200                 205 taa                                                                  627

<210> SEQ ID NO 4
<211> LENGTH: 208
<212> TYPE: PRT
<213> ORGANISM: Shigella flexneri
```

```
<400> SEQUENCE: 4

Met Lys Lys Ile Trp Leu Ala Leu Ala Gly Leu Val Leu Ala Phe Ser
 1               5                  10                  15

Ala Ser Ala Ala Gln Tyr Glu Asp Gly Lys Gln Tyr Thr Thr Leu Glu
            20                  25                  30

Lys Pro Val Ala Gly Ala Pro Gln Val Leu Glu Phe Phe Ser Phe Phe
        35                  40                  45

Cys Pro His Cys Tyr Gln Phe Glu Glu Val Leu His Ile Ser Asp Asn
    50                  55                  60

Val Lys Lys Leu Pro Glu Gly Val Lys Met Thr Lys Tyr His Val
65                  70                  75                  80

Asn Phe Met Gly Gly Asp Leu Gly Lys Asp Leu Thr Gln Ala Trp Ala
                85                  90                  95

Val Ala Met Ala Leu Gly Val Glu Asp Lys Val Thr Val Pro Leu Phe
            100                 105                 110

Glu Gly Val Gln Lys Thr Gln Thr Ile Arg Ser Ala Ser Asp Ile Arg
        115                 120                 125

Asp Val Phe Ile Asn Ala Gly Ile Lys Gly Glu Glu Tyr Asp Ala Ala
    130                 135                 140

Trp Asn Ser Phe Val Val Lys Ser Leu Val Ala Gln Gln Glu Lys Ala
145                 150                 155                 160

Ala Ala Asp Val Gln Leu Arg Gly Val Pro Ala Met Phe Val Asn Gly
                165                 170                 175

Lys Tyr Gln Leu Asn Pro Gln Gly Met Asp Thr Ser Asn Met Asp Val
            180                 185                 190

Phe Val Gln Gln Tyr Ala Asp Thr Val Lys Tyr Leu Ser Glu Glu Lys
        195                 200                 205

<210> SEQ ID NO 5
<211> LENGTH: 624
<212> TYPE: DNA
<213> ORGANISM: Klebsiella pneumoniae
<220> FEATURE:
<221> NAME/KEY: CDS
<222> LOCATION: (1)..(624)

<400> SEQUENCE: 5 atg aaa aaa gtt tgg ctg gcg ctg gct ggt atg att ctg gct ttt agt    48
Met Lys Lys Val Trp Leu Ala Leu Ala Gly Met Ile Leu Ala Phe Ser
 1               5                  10                  15 gca tcc gct gcc cag atc acc gac ggc aag cag tac atc acc ctt gat    96
Ala Ser Ala Ala Gln Ile Thr Asp Gly Lys Gln Tyr Ile Thr Leu Asp
            20                  25                  30 aag cct att gct ggc gag ccg cag gtg ctc gag ttc ttt tcg ttc tac   144
Lys Pro Ile Ala Gly Glu Pro Gln Val Leu Glu Phe Phe Ser Phe Tyr
        35                  40                  45 tgc ccg cac tgc tac cag ttt gaa gaa gtg ctg cat gtc tct gac aat   192
Cys Pro His Cys Tyr Gln Phe Glu Glu Val Leu His Val Ser Asp Asn
    50                  55                  60 gtg cgc cag aaa ctg ccg gaa ggc act aaa atg acc aaa tac cac gtt   240
Val Arg Gln Lys Leu Pro Glu Gly Thr Lys Met Thr Lys Tyr His Val
65                  70                  75                  80 gag ttc ctg ggt ccg ctg ggc aag gat ctg acg cag gca tgg gcg gtg   288
Glu Phe Leu Gly Pro Leu Gly Lys Asp Leu Thr Gln Ala Trp Ala Val
                85                  90                  95 gcc atc gcg ctg ggc gtt gaa gac aaa att act gcg ccg atg ttc gaa   336
Ala Ile Ala Leu Gly Val Glu Asp Lys Ile Thr Ala Pro Met Phe Glu
            100                 105                 110
```

```
gcc gtg cag aaa aac cag act gtg cag agt gtg gct gac att cgt aaa    384
Ala Val Gln Lys Asn Gln Thr Val Gln Ser Val Ala Asp Ile Arg Lys
            115                 120                 125 gtg ttt gtc gac gct ggc gta aaa ggg gaa gac tac gat gcc gca tgg    432
Val Phe Val Asp Ala Gly Val Lys Gly Glu Asp Tyr Asp Ala Ala Trp
130                 135                 140 aat agc ttc gtg gtg aaa tct ctg gtc gct cag caa gag aaa gcg gca    480
Asn Ser Phe Val Val Lys Ser Leu Val Ala Gln Gln Glu Lys Ala Ala
145                 150                 155                 160 gcc gat ctg cag ctg cag ggc gta ccg gct atg tat gtt aat ggt aaa    528
Ala Asp Leu Gln Leu Gln Gly Val Pro Ala Met Tyr Val Asn Gly Lys
            165                 170                 175 tac cag ctg aat ccg cag ggg atg gac acc agc aat atg gat gtc ttc    576
Tyr Gln Leu Asn Pro Gln Gly Met Asp Thr Ser Asn Met Asp Val Phe
        180                 185                 190 gtc gct cag tat gcg gat acc gtg aag caa ctg gta gag aag aaa taa    624
Val Ala Gln Tyr Ala Asp Thr Val Lys Gln Leu Val Glu Lys Lys
            195                 200                 205
```

<210> SEQ ID NO 6
<211> LENGTH: 207
<212> TYPE: PRT
<213> ORGANISM: Klebsiella pneumoniae

<400> SEQUENCE: 6

```
Met Lys Lys Val Trp Leu Ala Leu Ala Gly Met Ile Leu Ala Phe Ser
1               5                   10                  15

Ala Ser Ala Ala Gln Ile Thr Asp Gly Lys Gln Tyr Ile Thr Leu Asp
                20                  25                  30

Lys Pro Ile Ala Gly Glu Pro Gln Val Leu Glu Phe Phe Ser Phe Tyr
            35                  40                  45

Cys Pro His Cys Tyr Gln Phe Glu Glu Val Leu His Val Ser Asp Asn
        50                  55                  60

Val Arg Gln Lys Leu Pro Glu Gly Thr Lys Met Thr Lys Tyr His Val
65                  70                  75                  80

Glu Phe Leu Gly Pro Leu Gly Lys Asp Leu Thr Gln Ala Trp Ala Val
                85                  90                  95

Ala Ile Ala Leu Gly Val Glu Asp Lys Ile Thr Ala Pro Met Phe Glu
            100                 105                 110

Ala Val Gln Lys Asn Gln Thr Val Gln Ser Val Ala Asp Ile Arg Lys
        115                 120                 125

Val Phe Val Asp Ala Gly Val Lys Gly Glu Asp Tyr Asp Ala Ala Trp
130                 135                 140

Asn Ser Phe Val Val Lys Ser Leu Val Ala Gln Gln Glu Lys Ala Ala
145                 150                 155                 160

Ala Asp Leu Gln Leu Gln Gly Val Pro Ala Met Tyr Val Asn Gly Lys
                165                 170                 175

Tyr Gln Leu Asn Pro Gln Gly Met Asp Thr Ser Asn Met Asp Val Phe
            180                 185                 190

Val Ala Gln Tyr Ala Asp Thr Val Lys Gln Leu Val Glu Lys Lys
        195                 200                 205
```

<210> SEQ ID NO 7
<211> LENGTH: 624
<212> TYPE: DNA
<213> ORGANISM: Yersinia enterocolitica
<220> FEATURE:
<221> NAME/KEY: CDS
<222> LOCATION: (1)..(624)

```
<400> SEQUENCE: 7 atg aaa aat gta tgg tta gca ctc gtt ggc atg gtg atg gca ttc agt      48
Met Lys Asn Val Trp Leu Ala Leu Val Gly Met Val Met Ala Phe Ser
1               5                   10                  15 gca tcg gct gca caa ttt act gat ggt acc cag tac caa acg tta aac      96
Ala Ser Ala Ala Gln Phe Thr Asp Gly Thr Gln Tyr Gln Thr Leu Asn
            20                  25                  30 aaa ccg gta acc ggt gag ccc caa gtt tta gag ttt ttc tct ttc tat     144
Lys Pro Val Thr Gly Glu Pro Gln Val Leu Glu Phe Phe Ser Phe Tyr
        35                  40                  45 tgc ccg cac tgc tac cag ttt gaa gag gtt tac cat gtt cct caa gcg     192
Cys Pro His Cys Tyr Gln Phe Glu Glu Val Tyr His Val Pro Gln Ala
50                  55                  60 gta aag aaa gca ctg ccg gaa ggg act aaa atg act cgc tac cat gtt     240
Val Lys Lys Ala Leu Pro Glu Gly Thr Lys Met Thr Arg Tyr His Val
65                  70                  75                  80 gag ttc ctt ggc cca ttg ggc aag caa cta act caa gca tgg gct gtt     288
Glu Phe Leu Gly Pro Leu Gly Lys Gln Leu Thr Gln Ala Trp Ala Val
                85                  90                  95 gct atg gca ttg ggc gtt gaa gag aaa atc act cca ttg atg ttt gaa     336
Ala Met Ala Leu Gly Val Glu Glu Lys Ile Thr Pro Leu Met Phe Glu
            100                 105                 110 ggt gta cag aaa aca caa acg gta caa acc cct gat gat atc cgt aat     384
Gly Val Gln Lys Thr Gln Thr Val Gln Thr Pro Asp Asp Ile Arg Asn
        115                 120                 125 gta ttt atc aaa gca gga gtg agt ggt gaa gaa ttt gat gca gca tta     432
Val Phe Ile Lys Ala Gly Val Ser Gly Glu Glu Phe Asp Ala Ala Leu
130                 135                 140 aac agt ttt gtc gtt aaa tct ctg gtt gtt cag cag caa aaa gca gct     480
Asn Ser Phe Val Val Lys Ser Leu Val Val Gln Gln Gln Lys Ala Ala
145                 150                 155                 160 gaa gac tta gaa cta cgt ggt gta cca gcc atg ttt gtt aat ggc aaa     528
Glu Asp Leu Glu Leu Arg Gly Val Pro Ala Met Phe Val Asn Gly Lys
                165                 170                 175 tat atg att aaa aac gat ggc atg gat acc agc tca atg gat acc tat     576
Tyr Met Ile Lys Asn Asp Gly Met Asp Thr Ser Ser Met Asp Thr Tyr
            180                 185                 190 gtt aaa cag tat gca gat gtc gtt aag ttc ctg ctg act cag aaa taa     624
Val Lys Gln Tyr Ala Asp Val Val Lys Phe Leu Leu Thr Gln Lys
        195                 200                 205

<210> SEQ ID NO 8
<211> LENGTH: 207
<212> TYPE: PRT
<213> ORGANISM: Yersinia enterocolitica

<400> SEQUENCE: 8

Met Lys

```
                    Ala Met Ala Leu Gly Val Glu Glu Lys Ile Thr Pro Leu Met Phe Glu
                            100                 105                 110

Gly Val Gln Lys Thr Gln Thr Val Gln Thr Pro Asp Asp Ile Arg Asn
                            115                 120                 125

Val Phe Ile Lys Ala Gly Val Ser Gly Glu Glu Phe Asp Ala Ala Leu
                            130                 135                 140

Asn Ser Phe Val Val Lys Ser Leu Val Val Gln Gln Gln Lys Ala Ala
                    145                 150                 155                 160

Glu Asp Leu Glu Leu Arg Gly Val Pro Ala Met Phe Val Asn Gly Lys
                                    165                 170                 175

Tyr Met Ile Lys Asn Asp Gly Met Asp Thr Ser Ser Met Asp Thr Tyr
                            180                 185                 190

Val Lys Gln Tyr Ala Asp Val Val Lys Phe Leu Leu Thr Gln Lys
                            195                 200                 205

<210> SEQ ID NO 9
                    <211> LENGTH: 624
                    <212> TYPE: DNA
                    <213> ORGANISM: Photorhabdus luminescens
                    <220> FEATURE:
                    <221> NAME/KEY: CDS
                    <222> LOCATION: (1)..(624)

<400> SEQUENCE: 9 atg aag aag ttg tgg tta gct tta gtc gga atg gtt atg gca ttt agc       48
                    Met Lys Lys Leu Trp Leu Ala Leu Val Gly Met Val Met Ala Phe Ser
                    1               5                   10                  15 gta tct gcc gcc aat ttt act gaa gga aaa cag tat gtt gaa ttg aaa       96
                    Val Ser Ala Ala Asn Phe Thr Glu Gly Lys Gln Tyr Val Glu Leu Lys
                                    20                  25                  30 tcg ccg gta gcg gat caa cca ccg gtg cta gaa ttc ttc tct ttc tat      144
                    Ser Pro Val Ala Asp Gln Pro Pro Val Leu Glu Phe Phe Ser Phe Tyr
                                35                  40                  45 tgt ccc cat tgt tat cag ttt gaa gag att ttt aaa gtg cct cag acg      192
                    Cys Pro His Cys Tyr Gln Phe Glu Glu Ile Phe Lys Val Pro Gln Thr
                        50                  55                  60 gtg aaa cag cat tta ccg gaa ggg aca aaa ctt gtc cgt tat cat gtg      240
                    Val Lys Gln His Leu Pro Glu Gly Thr Lys Leu Val Arg Tyr His Val
                    65                  70                  75                  80 gat ttt tta ggg cca ctg ggt aaa gaa ttg act act gct tgg gct gcg      288
                    Asp Phe Leu Gly Pro Leu Gly Lys Glu Leu Thr Thr Ala Trp Ala Ala
                                    85                  90                  95 gca atg gca atg ggt gtt gaa gac aaa gtg act ccg gtg ctg ttt gag      336
                    Ala Met Ala Met Gly Val Glu Asp Lys Val Thr Pro Val Leu Phe Glu
                                    100                 105                 110 ggg att cag aaa aca ctg gct att aag act ccg aat gat att cgc aat      384
                    Gly Ile Gln Lys Thr Leu Ala Ile Lys Thr Pro Asn Asp Ile Arg Asn
                                    115                 120                 125 gct ttt atc aaa gcc ggg gtg act gct gag gat tat gat gct gct atg      432
                    Ala Phe Ile Lys Ala Gly Val Thr Ala Glu Asp Tyr Asp Ala Ala Met
                            130                 135                 140 agc agt ttt gtg gtg aaa tcc tta gtt gtt aag cag caa aaa gcc gct      480
                    Ser Ser Phe Val Val Lys Ser Leu Val Val Lys Gln Gln Lys Ala Ala
                    145                 150                 155                 160 cag gat ttg caa ttg cga ggt gta ccg gca atg ttt gtt aac ggc aag      528
                    Gln Asp Leu Gln Leu Arg Gly Val Pro Ala Met Phe Val Asn Gly Lys
                                    165                 170                 175 tat atg gtg aaa aat gac ggc att gat gcc act tct gct gat aac tat      576
                    Tyr Met Val Lys Asn Asp Gly Ile Asp Ala Thr Ser Ala Asp Asn Tyr
                            180                 185                 190
```

-continued

```
gcg aaa ccc tat tca gat gtt gtt aac ttc ttg tta agt cag aag taa      624
Ala Lys Pro Tyr Ser Asp Val Val Asn Phe Leu Leu Ser Gln Lys
        195                 200                 205

<210> SEQ ID NO 10
<211> LENGTH: 207
<212> TYPE: PRT
<213> ORGANISM: Photorhabdus luminescens

<400> SEQUENCE: 10

Met Lys Lys Leu Trp Leu Ala Leu Val Gly Met Val Met Ala Phe Ser
1               5                   10                  15

Val Ser Ala Ala Asn Phe Thr Glu Gly Lys Gln Tyr Val Glu Leu Lys
            20                  25                  30

Ser Pro Val Ala Asp Gln Pro Val Leu Glu Phe Ser Phe Tyr
        35                  40                  45

Cys Pro His Cys Tyr Gln Phe Glu Glu Ile Phe Lys Val Pro Gln Thr
    50                  55                  60

Val Lys Gln His Leu Pro Glu Gly Thr Lys Leu Val Arg Tyr His Val
65                  70                  75                  80

Asp Phe Leu Gly Pro Leu Gly Lys Glu Leu Thr Thr Ala Trp Ala Ala
                85                  90                  95

Ala Met Ala Met Gly Val Glu Asp Lys Val Thr Pro Val Leu Phe Glu
            100                 105                 110

Gly Ile Gln Lys Thr Leu Ala Ile Lys Thr Pro Asn Asp Ile Arg Asn
        115                 120                 125

Ala Phe Ile Lys Ala Gly Val Thr Ala Glu Asp Tyr Asp Ala Ala Met
    130                 135                 140

Ser Ser Phe Val Val Lys Ser Leu Val Val Lys Gln Gln Lys Ala Ala
145                 150                 155                 160

Gln Asp Leu Gln Leu Arg Gly Val Pro Ala Met Phe Val Asn Gly Lys
                165                 170                 175

Tyr Met Val Lys Asn Asp Gly Ile Asp Ala Thr Ser Ala Asp Asn Tyr
            180                 185                 190

Ala Lys Pro Tyr Ser Asp Val Val Asn Phe Leu Leu Ser Gln Lys
        195                 200                 205

<210> SEQ ID NO 11
<211> LENGTH: 621
<212> TYPE: DNA
<213> ORGANISM: Pasteurella multocida
<220> FEATURE:
<221> NAME/KEY: CDS
<222> LOCATION: (1)..(621)

<400> SEQUENCE: 11 atg aaa aaa tta gtt tta gcg gtg acg tca ttc ctt ttt gct gtt tct       48
Met Lys Lys Leu Val Leu Ala Val Thr Ser Phe Leu Phe Ala Val Ser
1               5                   10                  15 gta caa gcg aca aat tta acc gag ggt aag cag tat gtg acg tta aat      96
Val Gln Ala Thr Asn Leu Thr Glu Gly Lys Gln Tyr Val Thr Leu Asn
            20                  25                  30 cag gca cct gta caa caa gca gaa gtc atc gag ttt ttc tct ttt tat     144
Gln Ala Pro Val Gln Gln Ala Glu Val Ile Glu Phe Phe Ser Phe Tyr
        35                  40                  45 tgt cca cat tgt tat tcg ttt gaa tac gaa tac caa atc cca aat aaa     192
Cys Pro His Cys Tyr Ser Phe Glu Tyr Glu Tyr Gln Ile Pro Asn Lys
    50                  55                  60 gtg aaa cag cag ttg cca gaa ggt gtg agc ttg aaa caa tat cat gtc     240
Val Lys Gln Gln Leu Pro Glu Gly Val Ser Leu Lys Gln Tyr His Val
```

```
                      65                  70                  75                  80
aac ttt tta ggc ggt gaa atg ggg aaa aat ctt act cgt gca tgg gca                     288
Asn Phe Leu Gly Gly Glu Met Gly Lys Asn Leu Thr Arg Ala Trp Ala
                85                  90                  95 ttg gct atg gcg acc ggt gta caa gat aaa gta aaa gaa cct tta ttt                     336
Leu Ala Met Ala Thr Gly Val Gln Asp Lys Val Lys Glu Pro Leu Phe
            100                 105                 110 ttc gcg gca cag caa aat aaa tta cgc agt atg gat gat att cgt caa                     384
Phe Ala Ala Gln Gln Asn Lys Leu Arg Ser Met Asp Asp Ile Arg Gln
        115                 120                 125 atc ttt ttg gct aat ggt ctc agt gca gaa caa ttt gat ggc gga att                     432
Ile Phe Leu Ala Asn Gly Leu Ser Ala Glu Gln Phe Asp Gly Gly Ile
    130                 135                 140 aac agt ttt gcc gtc aca gcg tta acc aat aag caa gtg aca gcg gct                     480
Asn Ser Phe Ala Val Thr Ala Leu Thr Asn Lys Gln Val Thr Ala Ala
145                 150                 155                 160 gaa cac atg aaa gtg cgt ggt gtg cca gat ttt tac gta aac ggg cgt                     528
Glu His Met Lys Val Arg Gly Val Pro Asp Phe Tyr Val Asn Gly Arg
                165                 170                 175 tat cgt gtt aat cct gaa gga ctg aaa aac gac agc cat gaa gcg ttt                     576
Tyr Arg Val Asn Pro Glu Gly Leu Lys Asn Asp Ser His Glu Ala Phe
            180                 185                 190 gtt gct gat tat gtc gaa aca gta aaa ggt tta ttg caa aaa taa                         621
Val Ala Asp Tyr Val Glu Thr Val Lys Gly Leu Leu Gln Lys
        195                 200                 205

<210> SEQ ID NO 12
<211> LENGTH: 206
<212> TYPE: PRT
<213> ORGANISM: Pasteurella multocida

<400> SEQUENCE: 12

Met Lys Lys Leu Val Leu Ala Val Thr Ser Phe Leu Phe Ala Val Ser
1               5                   10                  15

Val Gln Ala Thr Asn Leu Thr Glu Gly Lys Gln Tyr Val Thr Leu Asn

```
<210> SEQ ID NO 13
<211> LENGTH: 35
<212> TYPE: DNA
<213> ORGANISM: Artificial Sequence
<220> FEATURE:
<223> OTHER INFORMATION: primer

<400> SEQUENCE: 13
cgcggatcca atggtcataa atggcagcgt agcgc                              35

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
cgcggatccg cagggcgttg cggaacaaac                                    30
```

L-CYSTEINE-PRODUCING BACTERIUM AND A METHOD FOR PRODUCING L-CYSTEINE

This application claims priority under 35 U.S.C. §119 to Japanese Patent Application No. 2009-042561, filed on Feb. 25, 2009, and U.S. Provisional Patent Application No. 61/155,513, filed on Feb. 25, 2009, both of which are incorporated in their entireties by reference. The Sequence Listing in electronic format filed herewith is also hereby incorporated by reference in its entirety (File Name: US-388_Seq_List; File Size: 30 KB; Date Created: Feb. 23, 2010).

BACKGROUND OF THE INVENTION

1. Field of the Invention

The present invention relates to a method for producing L-cysteine or related substances. Specifically, the present invention relates to a bacterium suitable for the production of L-cysteine or related substances and a method for producing L-cysteine or related substances utilizing such a bacterium. L-cysteine and L-cysteine related substances are useful in the fields of drugs, cosmetics, and foods.

2. Brief Description of the Related Art

L-cysteine is conventionally obtained by extraction from keratin-containing substances such as hair, horns, and feathers, or by the conversion of DL-2-aminothiazoline-4-carboxylic acid using a microbial enzyme. L-cysteine has also been produced on a large scale by using an immobilized enzyme method and a novel enzyme. Furthermore, it has also been attempted to produce L-cysteine by fermentation utilizing a microorganism.

Microorganisms which are able to produce L-cysteine are known. For example, a coryneform bacterium with increased intracellular serine acetyltransferase activity produces cysteine (Japanese Patent Laid-open (Kokai) No. 2002-233384). The ability to produce L-cysteine can also be increased by incorporating serine acetyltransferase which has been mutated to attenuate feedback inhibition by L-cysteine (Japanese Patent Laid-open No. 11-155571, U.S. Patent Published Application No. 20050112731, U.S. Pat. No. 6,218,168).

Furthermore, the ability to produce L-cysteine in a microorganism can be enhanced by suppressing the L-cysteine decomposition system. Examples of such microorganisms include coryneform bacteria or *Escherichia* bacteria in which the activity of cystathionine-β-lyase (Japanese Patent Laid-open No. 11-155571), tryptophanase (Japanese Patent Laid-open No. 2003-169668), or O-acetylserine sulfhydrylase B (Japanese Patent Laid-open No. 2005-245311) is attenuated or deleted.

Furthermore, it is known that the ydeD gene which encodes the YdeD protein participates in secretion of the metabolic products of the cysteine pathway (Dabler et al., Mol. Microbiol., 36, 1101-1112 (2000)). Furthermore, techniques for enhancing the ability to produce L-cysteine by increasing expression of the mar-locus, emr-locus, acr-locus, cmr-locus, mex-gene, bmr-gene or qacA-gene are also known. These loci and/or genes encode proteins which cause secretion of toxic substances from cells (U.S. Pat. No. 5,972,663). emrAB, emrKY, yojIH, acrEF, bcr, and cusA are further examples (Japanese Patent Laid-open No. 2005-287333).

An *Escherichia coli* has been reported which produces L-cysteine, and which has increased activity of the positive transcriptional control factor of the cysteine regulon encoded by the cysB gene (International Patent Publication WO01/27307).

It is known that dsbA (Shevchik V. E., et al., EMBO J., 1994 Apr. 15; 13(8):2007-12) participates in the formation of disulfide bonds (S—S) of proteins as described below, but the relation thereof with L-cysteine production is not known.

In general, many proteins with a disulfide bond (S—S) are among proteins that are secreted into cell membrane surface layers or out of cells. The interior of cells enclosed by the cell membranes is under relatively mild conditions both physically and chemically. However, since the exterior of cells is a more severe environment, the structures of proteins need to be more rigid. The presence of S—S bonds in proteins is one of the strategies.

Anfinsen et al. demonstrated that oxidative folding of proteins accompanied by the formation of S—S bonds spontaneously advanced under moderate oxidative conditions (Givol D. et al., J. Biol. Chem., 1964, Sep.; 239:PC3114-16). However, it has been elucidated that, in a cell, there is a delicate system for the formation of S—S bond, so that it can advance more quickly and correctly as compared with the aforementioned formation of S—S bonds (Bardwell J. C., et al., Cell, 1991 Nov. 1; 67(3):581-9.). For example, in the periplasm of *Escherichia coli*, a series of proteins called Dsb factors (disulfide bond, DsbA, DsbB, DsbC (Shevchik V. E., et al., EMBO J., 1994 Apr. 15; 13(8):2007-12), DsbD (Missiakas D., et al., EMBO J., 1995 Jul. 17; 14(14):3415-24), and DsbG (Andersen C. L., et al., Mol. Microbiol., 1997, Oct.; 26(1):121-32)) form disulfide bonds and introduce them into many proteins. In the periplasm, DsbA (disulfide oxidoreductase) oxidizes a substrate protein (AmpC, DsbB, LivK, OstA, RcsF (Kadokura H., et al., Science, 2004, Jan. 23; 303(5657): 534-7)), and the cysteine pair of DsbA converted into the reduced type is re-oxidized with the intracellular membrane protein DsbB. It has been elucidated that electrons received by DsbB are transferred to ubiquinone (UQ), which is a respiratory chain component, and oxygen eventually serves as an electron acceptor with the aid of cytochrome oxidase (Inaba K., et al., J. Biol. Chem., 279, 6761-6768 (2004)).

Although DsbA has superior characteristics as an S—S bond-introducing enzyme, the ability thereof to select a cysteine pair into which the bond is introduced is not sufficient. It has also been found that the enzyme DsbC (disulfide isomerase) which recombines incorrect S—S bonds is present in the periplasm of *Escherichia coli*. In order for DsbC to function as an isomerase, the active site thereof must be maintained as a reduced type, contrary to DsbA, which is an oxidase. It is considered that the source of the reducing power originates in the thioredoxin system existing in the cytoplasm, and the reducing power from thioredoxin is transferred to DsbC via an intracellular membrane protein DsbD (Rietsch A., et al., J. Bacteriol., 1997 November; 179(21): 6602-8). Moreover, it is also considered that a protein called DsbG which shows narrower substrate specificity is also present in *Escherichia coli*, and it has activities of both disulfide oxidoreductase and disulfide isomerase (Andersen C. L., et al., Mol. Microbiol., 1997, Oct.; 26(1):121-32).

As for the use of the aforementioned Dsb family, there are such findings as mentioned below, with expecting the effect of correctly forming S—S bonds of proteins. Many proteins derived from eukaryotic organisms have a disulfide bond, and they cannot be expected to have their original structures when they are expressed in the cytoplasm of *Escherichia coli*, which is under severe reducing conditions. Therefore, it is considered that, for production of such proteins derived from eukaryotic organisms, expression in the form of secretion into the periplasm is effective, which is under an oxidative environment preferred for formation of disulfide bond. However, although many attempts of expressing heterogenous proteins by secretion into *Escherichia coli* periplasm have been reported, any heterogenous protein cannot necessarily be expressed as active proteins. This poses a problem especially for proteins having many disulfide bonds. Meanwhile, in *Escherichia coli*, the roles of DsbA, DsbB, DsbC, and DsbD, which are the Dsb family proteins involved in the formation of disulfide bond, were deduced on the basis of biochemical tests and complementation tests using strains deficient in each of the genes (Bardwell, J. C., Mol. Microbiol., 14, 199-205 (1994), Sone, M., et al., J. Biol. Chem., 272, 10349-10352 (1997), Rietsch, A., et al., Proc. Natl. Acad. Sci. USA, 93, 13048-13053 (1996)). Therefore, there have been made several attempts of overexpressing DsbA or DsbC together with an objective protein with the goal of improving the secretion expression of the objective protein into the periplasm (Japanese Patent Laid-open No. 2000-83670). Furthermore, it is also already known that DsbA works as a re-activating agent for proteins that do not have physiological activity (Akiyama Y., et al., J. Biol. Chem., 1992 Nov. 5; 267(31):22440-5, Japanese Patent Laid-open No. 5-336986). However, only the oxidation of proteins has been described in the reports to date, and there is no example of reporting involvement of the Dsb factors in oxidation of low molecules such as amino acids. Therefore, it has been completely unknown whether the Dsb factors oxidize low molecular weight molecules such as cysteine to form cystine.

SUMMARY OF THE INVENTION

The present invention provides a novel technique for improving bacterial production of L-cysteine, and thereby provides an L-cysteine-producing bacterium, as well as a method for producing L-cysteine, L-cystine, their derivatives or precursors, or a mixture of these by using such a bacterium.

L-cysteine-producing ability of a bacterium is enhanced by modifying the bacterium so that the activity of the protein encoded by the dsbA gene is increased.

It is an aspect of the present invention to provide a bacterium belonging to the family Enterobacteriaceae, which is able to produce L-cysteine and has been modified to increase the activity of the protein encoded by the dsbA gene as compared to a non-modified bacterium.

It is a further aspect of the present invention to provide the bacterium as described above, wherein the activity of the protein is increased by a method selected from the group consisting of 1) increasing expression of the dsbA gene, 2) increasing translation of the dsbA gene, and 3) combination thereof.

It is a further aspect of the present invention to provide the bacterium as described above, wherein expression of the dsbA gene is increased by increasing the copy number of the dsbA gene or by modifying an expression control sequence of the gene.

It is a further aspect of the present invention to provide the bacterium as described above, wherein the protein is selected from the group consisting of:

(A) a protein comprising the amino acid sequence of SEQ ID NO: 2, 4, 6, 8, 10 or 12, (B) a protein comprising the amino acid sequence of SEQ ID NO: 2, 4, 6, 8, 10 or 12, but which includes substitutions, deletions, insertions or additions of one or several amino acid residues, and wherein the increase of the protein's activity in the bacterium improves the ability of the bacterium to produce L-cysteine.

It is a further aspect of the present invention to provide the bacterium as described above, wherein the dsbA gene is selected from the group consisting of:

(a) a DNA comprising the nucleotide sequence of SEQ ID NO: 1, 3, 5, 7, 9 or 11, (b) a DNA which hybridizes with a sequence complementary to the nucleotide sequence of SEQ ID NO: 1, 3, 5, 7, 9 or 11, or a probe which is prepared from the nucleotide sequence, under stringent conditions, and codes for a protein wherein the increase of the protein's activity in the bacterium improves the ability of the protein to produce L-cysteine.

It is a further aspect of the present invention to provide the bacterium as described above, which contains a serine acetyltransferase which has been mutated to attenuate feedback inhibition by L-cysteine.

It is a further aspect of the present invention to provide the bacterium as described above, wherein the bacterium has been modified so that the activity of the protein encoded by the ydeD gene is increased.

It is a further aspect of the present invention to provide the bacterium as described above, wherein 3-phosphoglycerate dehydrogenase has been desensitized to feedback inhibition by serine.

It is a further aspect of the present invention to provide the bacterium as described above, wherein bacterium has been modified so that the activity of the protein encoded by the ydeD gene is increased.

It is a further aspect of the present invention to provide the bacterium as described above, which is an *Escherichia* bacterium.

It is a further aspect of the present invention to provide the bacterium as described above, which is *Escherichia coli*.

It is a further aspect of the present invention to provide a method for producing a compound selected from the group consisting of L-cysteine, L-cystine, and derivatives or precursors thereof, which comprises culturing the bacterium as described above in a medium and collecting the compound from the medium.

It is a further aspect of the present invention to provide the method as described above, wherein the derivative of L-cysteine is a thiazolidine derivative.

It is a further aspect of the present invention to provide the method as described above, wherein the precursor of L-cysteine is O-acetylserine or N-acetylserine.

According to the present invention, L-cysteine-producing ability of bacteria can be improved. Furthermore, according to the present invention, L-cysteine, L-cystine, their derivatives or precursors, or combinations thereof can be efficiently produced.

Still other aspects, features, and attendant advantages of the present invention will become apparent to those skilled in the art from a reading of the following detailed description of embodiments constructed in accordance therewith, taken in conjunction with the accompanying drawings.

DETAILED DESCRIPTION OF EXEMPLARY EMBODIMENTS

<1> Bacterium

Figure 1:
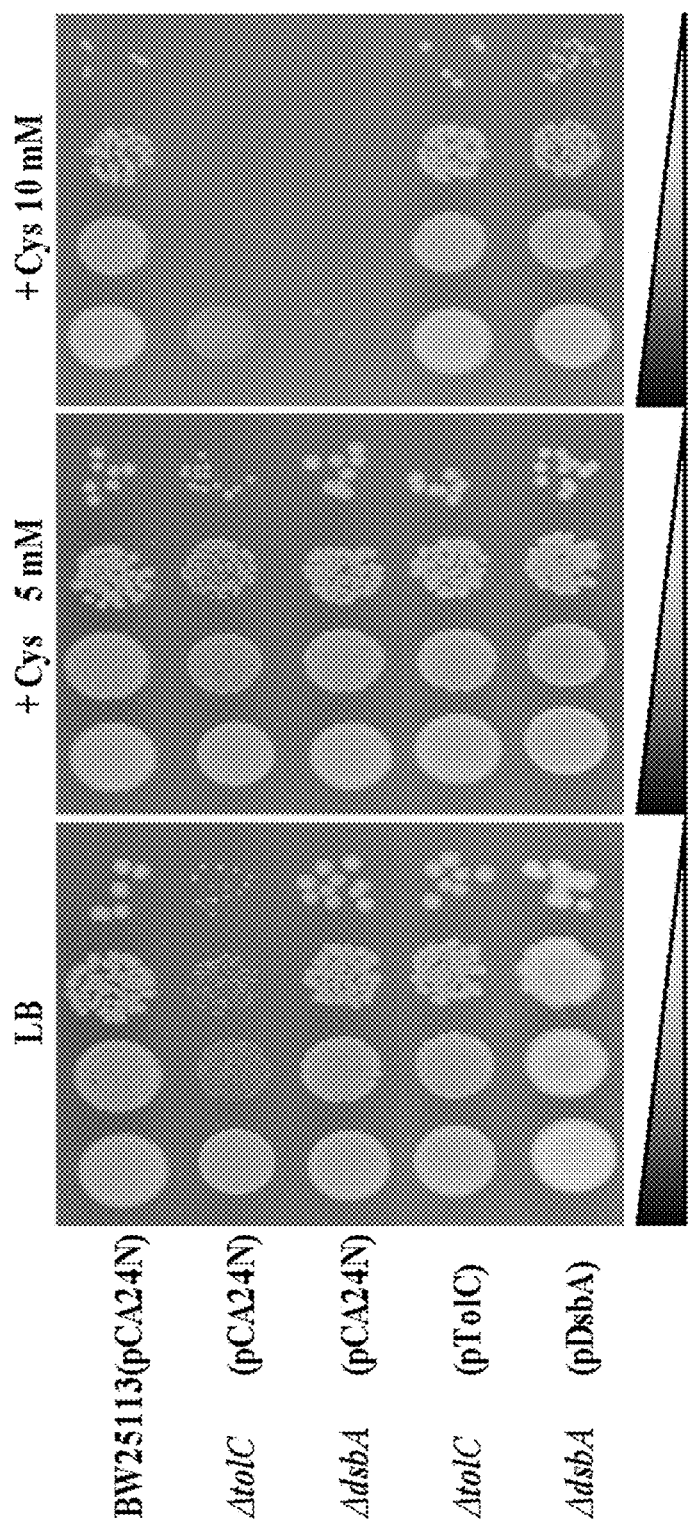
FIG. 1 shows cysteine sensitivity of a dsbA-deficient strain and complementation (recovery of growth) with a dsbA plasmid (photograph).

The bacterium belongs to the family Enterobacteriaceae, and is able to produce L-cysteine. Furthermore, the bacterium has been modified to increase the activity of the protein encoded by the dsbA gene. The "ability to produce L-cysteine" or the "L-cysteine-producing ability" means an ability of the bacterium to produce L-cysteine and cause accumulation of L-cysteine in a medium or the bacterial cells in such an amount that the L-cysteine can be collected from the medium or cells when the bacterium is cultured in the medium. A bacterium having L-cysteine-producing ability means a bacterium which can produce and cause accumulation of a larger amount of L-cysteine as compared with a wild-type, parent, or unmodified strain, for example, a bacterium which can produce and cause accumulation of L-cysteine in a medium in an amount of 0.05 g/L or more, 0.1 g/L or more, or even 0.2 g/L or more.

The L-cysteine produced by the bacterium can change into L-cystine in the medium by the formation of a disulfide bond. Especially, as described later, it is considered that if L-cysteine is produced in a large amount by enhancing the DsbA activity, formation of L-cystine from L-cysteine by the DsbA-DsbB-UQ oxidation system is promoted. Furthermore, S-sulfocysteine can be generated by the reaction of L-cysteine and thiosulfuric acid in the medium (Szczepkowski T. W., Nature, vol. 182 (1958)). Furthermore, the L-cysteine generated in bacterial cells can be condensed with a ketone, aldehyde, or, for example, pyruvic acid, which is present in the cells, to produce a thiazolidine derivative via a hemithioketal intermediate (refer to Japanese Patent No. 2992010). This thiazolidine derivative and hemithioketal can be present as an equilibrated mixture. Therefore, the L-cysteine-producing ability is not limited to the ability to accumulate only L-cysteine in the medium or cells, but also includes the ability to accumulate L-cystine or its derivatives or precursors, or a mixture thereof in the medium. Examples of the aforementioned derivative of L-cysteine or L-cystine include, for example, S-sulfocysteine, thiazolidine derivatives, hemithioketal, and so forth. Examples of the precursor of L-cysteine or L-cystine include, for example, O-acetylserine, which is a precursor of L-cysteine. The precursors of L-cysteine or L-cystine also include derivatives of the precursors, and examples include, for example, N-acetylserine, which is a derivative of O-acetylserine, and so forth.

O-Acetylserine (OAS) is a precursor of L-cysteine biosynthesis. OAS is a metabolite of bacteria and plants, and is produced by acetylation of L-serine by an enzymatic reaction catalyzed by serine acetyltransferase (SAT). OAS is further converted into L-cysteine in cells.

The bacterium having L-cysteine-producing ability can inherently have the ability to produce L-cysteine, or it can be imparted by modifying a microorganism such as those described below by mutagenesis or a recombinant DNA technique. Unless specially mentioned, the term L-cysteine refers to the reduced-type L-cysteine, L-cystine, a derivative or precursor such as those mentioned above, or a mixture thereof.

The bacterium is not particularly limited so long as the bacterium belongs to the family Enterobacteriaceae and has L-cysteine-producing ability. Such bacteria include those of the genera *Escherichia, Enterobacter, Pantoea, Klebsiella, Serratia, Erwinia, Salmonella* and *Morganella*. Specifically, those classified into the family Enterobacteriaceae according to the taxonomy used in the NCBI (National Center for Biotechnology Information) database (http://www.ncbi.nlm.nih.gov/Taxonomy/Browser/wwwtax.cgi?id=91347) can be used. As the parent strain of the family Enterobacteriaceae which can be used to perform modification, it is desirable to use, especially, a bacterium of the genus *Escherichia, Enterobacter, Pantoea, Erwinia*, or *Klebsiella*.

Although the *Escherichia* bacteria are not particularly limited, specifically, those described in the work of Neidhardt et al. (Backmann B. J., 1996, Derivations and Genotypes of some mutant derivatives of *Escherichia coli* K-12, p. 2460-2488, Table 1, In F. D. Neidhardt (ed.), *Escherichia coli* and *Salmonella* Cellular and Molecular Biology/Second Edition, American Society for Microbiology Press, Washington, D.C.) can be used. An example of *Escherichia* bacterium includes *Escherichia coli*. Examples of *Escherichia coli* include *Escherichia coli* W3110 (ATCC 27325), *Escherichia coli* MG1655 (ATCC 47076), and so forth, and include those derived from the prototype wild-type strain, K12 strain.

These strains are available from, for example, the American Type Culture Collection (Address: 12301 Parklawn Drive, Rockville, Md. 20852, P.O. Box 1549, Manassas, Va. 20108, United States of America). That is, registration numbers are given to each of the strains, and the strains can be ordered by using these registration numbers (refer to http://www.atcc.org/). The registration numbers of the strains are listed in the catalogue of the American Type Culture Collection.

Examples of the *Enterobacter* bacteria include *Enterobacter agglomerans, Enterobacter aerogenes* and so forth, and examples of the *Pantoea* bacteria include *Pantoea ananatis*. Some strains of *Enterobacter agglomerans* were recently reclassified into *Pantoea agglomerans, Pantoea ananatis*, or *Pantoea stewartii* on the basis of nucleotide sequence analysis of 16S rRNA etc. A bacterium belonging to either *Enterobacter* or *Pantoea* can be used so long as it is classified as the family Enterobacteriaceae.

In particular, *Pantoea* bacteria, *Erwinia* bacteria, and *Enterobacter* bacteria are classified as γ-proteobacteria, and they are taxonomically very close to one another (J. Gen. Appl. Microbiol., 1997, 43, 355-361; International Journal of Systematic Bacteriology, October 1997, pp. 1061-1067). In recent years, some bacteria belonging to the genus *Enterobacter* were reclassified as *Pantoea agglomerans, Pantoea dispersa*, or the like, on the basis of DNA-DNA hybridization experiments etc. (International Journal of Systematic Bacteriology, July 1989, 39(3), pp. 337-345). Furthermore, some bacteria belonging to the genus *Erwinia* were reclassified as *Pantoea ananas* or *Pantoea stewartii* (refer to International Journal of Systematic Bacteriology, January 1993; 43(1), pp. 162-1'73).

Examples of the *Enterobacter* bacteria include, but are not limited to, *Enterobacter agglomerans, Enterobacter aerogenes*, and so forth. Specifically, the strains exemplified in European Patent Publication No. 952221 can be used. A typical strain of the genus *Enterobacter* is the *Enterobacter agglomeranses* ATCC 12287 strain.

Typical strains of the *Pantoea* bacteria include, but are not limited to, *Pantoea ananatis, Pantoea stewartii, Pantoea agglomerans*, and *Pantoea citrea*. Specific examples of *Pantoea ananatis* include the *Pantoea ananatis* AJ13355 strain and SC17 strain. The SC17 strain was selected as a low phlegm-producing mutant strain from the AJ13355 strain (FERM BP-6614), which was isolated from soil in Iwata-shi, Shizuoka-ken, Japan for its ability to proliferate in a low pH medium containing L-glutamic acid and a carbon source (U.S. Pat. No. 6,596,517). The *Pantoea ananatis* AJ13355 strain was deposited at the National Institute of Bioscience and Human-Technology, Agency of Industrial Science and Technology, Ministry of International Trade and Industry (currently, the National Institute of Advanced Industrial Science and Technology, International Patent Organism Depositary, Address: Tsukuba Central 6, 1-1, Higashi 1-Chome, Tsukuba-shi, Ibaraki-ken, 305-8566, Japan) on Feb. 19, 1998 and assigned an accession number of FERM P-16644. It was then converted to an international deposit under the provisions of Budapest Treaty on Jan. 11, 1999 and assigned an accession number of FERM BP-6614. This strain was identified as *Enterobacter agglomerans* when it was isolated and deposited as the *Enterobacter agglomerans* AJ13355 strain. However, it was recently reclassified as *Pantoea ananatis* on the basis of nucleotide sequencing of 16S rRNA and so forth.

Examples of the *Erwinia* bacteria include, but are not limited to, *Erwinia amylovora* and *Erwinia carotovora*, and examples of the *Klebsiella* bacteria include *Klebsiella planticola*.

Hereinafter, methods for imparting L-cysteine-producing ability to bacteria belonging to Enterobacteriaceae, or methods for enhancing L-cysteine-producing ability of such bacteria, are described.

To impart the ability to produce L-cysteine, methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can be used. Such methods include by acquiring the properties of an auxotrophic mutant, an analogue-resistant strain, or a metabolic regulation mutant, or by constructing a recombinant strain so that it overexpresses an L-cysteine biosynthesis enzyme. Here, in the breeding of a bacteria able to produce L-cysteine, one or more of the above described properties such as auxotrophy, analogue resistance, and metabolic regulation mutation can be imparted. The expression of L-cysteine biosynthesis enzyme(s) can be enhanced alone or in combinations of two or more. Furthermore, imparting properties such as an auxotrophy, analogue resistance, or metabolic regulation mutation can be combined with enhancement of the biosynthesis enzymes.

An auxotrophic mutant strain, L-cysteine analogue-resistant strain, or metabolic regulation mutant strain with the ability to produce L-cysteine can be obtained by subjecting a parent, wild-type, or unmodified strain to conventional mutatagenesis, such as exposure to X-rays or UV irradiation, or by treating with a mutagen such as N-methyl-N'-nitro-N-nitrosoguanidine, ethyl methanesulfonate (EMS) etc., and then selecting those which exhibit autotrophy, analogue resistance, or a metabolic regulation mutation and which also have the ability to produce L-cysteine from the obtained transformants.

Specific examples of L-cysteine-producing bacteria include, but are not limited to, *E. coli* JM15 transformed with multiple kinds of cysE gene alleles encoding serine acetyltransferase (SAT) resistant to feedback inhibition (U.S. Pat. No. 6,218,168), *E. coli* W3110 in which a gene encoding a protein responsible for excretion of cytotoxic substances is overexpressed (U.S. Pat. No. 5,972,663), an *E. coli* strain having decreased cysteine desulfhydrase activity (Japanese Patent Laid-open No. 11-155571), and *E. coli* W3110 with decreased activity of the positive transcriptional control factor of the cysteine regulon encoded by the cysB gene (WO01/27307).

The following proteins are known to have the cysteine desulfhydrase activity of *E. coli*: cystathionine-β-lyase (metC product, Japanese Patent Laid-open No. 11-155571, Chandra et al., Biochemistry, 21 (1982) 3064-3069), tryptophanase (tnaA product, Japanese Patent Laid-open No. 2003-169668, Austin Newton et al., J. Biol. Chem., 240 (1965) 1211-1218)), O-acetylserine sulfhydrylase B (cysM gene product, Japanese Patent Laid-open No. 2005-245311) and the malY gene product (Japanese Patent Laid-open No. 2005-245311). By decreasing the activities of these proteins, L-cysteine-producing ability is improved. The phrase "decreasing activity of a protein" can mean that activity of the protein is decreased as compared with a non-modified strain such as a wild-type or parent strain, and also can mean the complete disappearance of the activity.

Decreasing the activity of a protein having the cysteine desulfhydrase activity can be attained by, for example, reducing expression of a gene coding for the protein. Specifically, for example, intracellular activity of the protein can be reduced by deleting a part of or the entire coding region of the target gene on the chromosome. Expression of a target gene can also be decreased by modifying an expression control sequence of the gene such as promoter and Shine-Dalgarno (SD) sequence. Furthermore, the expression of the gene can also be reduced by modifying a non-translated region other than the expression control sequence. Furthermore, the entire gene as well as the sequences on both sides of the gene on the chromosome can be deleted. Furthermore, a mutations which cause an amino acid substitution (missense mutation), a stop codon (nonsense mutation), or a frame shift mutation which adds or deletes one or two nucleotides into the coding region of the target gene on the chromosome can be introduced (Journal of Biological Chemistry, 272:8611-8617 (1997); Proceedings of the National Academy of Sciences, USA, 95 5511-5515 (1998); Journal of Biological Chemistry, 266, 20833-20839 (1991)).

Furthermore, modification can be caused by a conventional mutagenesis based on X-ray or ultraviolet irradiation or the use of a mutagen such as N-methyl-N'-nitro-N-nitrosoguanidine, as long as the activity of the target protein is decreased.

An expression control sequence can be modified by mutating one or more nucleotides, two or more nucleotides, or three or more nucleotides. Deletions can occur in the N-terminus region, an internal region, or the C-terminus region, or even the entire coding region, so long as the function of the target protein is decreased or deleted. The longer the region which is deleted, the greater the likelihood of inactivating the gene. Furthermore, the deleted reading frames upstream and downstream of the region can be the same or different.

To inactivate a gene by inserting a sequence into the coding region of the gene, the sequence can be inserted into any part of the coding region of the gene. The longer the inserted sequence, the greater the likelihood of inactivating the gene. The reading frames upstream and downstream of the insertion site can be the same or different. The sequence to be inserted is not particularly limited so long as the insertion decreases or deletes the function of the encoded protein, and examples include a transposon carrying an antibiotic resistance gene, a gene useful for L-cysteine production and so forth.

A target gene on the chromosome can be modified as described above by, for example, preparing a deletion-type version of the gene in which a partial sequence of the gene is deleted so that the deletion-type gene does not produce a normally-functioning proteins. Then, a bacterium can be transformed with a DNA containing the deletion-type gene to cause homologous recombination between the deletion-type gene and the native gene on the chromosome, which results in the substitution of the deletion-type gene for the gene on the genome. The protein encoded by the deletion-type gene has a conformation different from that of the wild-type enzyme protein, if it is even produced, and thus the function is reduced or deleted. Such gene disruption based on gene substitution utilizing homologous recombination is known, and examples include Red-driven integration (Datsenko, K. A., and Wanner, B. L., Proc. Natl. Acad. Sci. USA, 97:6640-6645 (2000)), using a linear DNA utilizing in Red driven integration in combination with an excision system derived from λ phage (Cho, E. H., Gumport, R. I., Gardner, J. F., J. Bacteriol., 184:5200-5203 (2002)) (refer to WO2005/010175), using a plasmid containing a temperature sensitive replication origin or a plasmid capable of conjugative transfer, utilizing a suicide vector without a replication origin in a host (U.S. Pat. No. 6,303,383, Japanese Patent Laid-open No. 05-007491), and so forth.

Decrease of the expression of a target gene can be confirmed by comparing the amount of mRNA transcribed from the gene with that in a wild-type strain or non-modified strain. The expression amount can be confirmed by Northern hybridization, RT-PCR (Molecular Cloning (Cold Spring Harbor Laboratory Press, Cold Spring Harbor (USA), 2001)), and the like.

A decrease of the amount of a target protein can be confirmed by Western blotting using antibodies (Molecular Cloning (Cold Spring Harbor Laboratory Press, Cold Spring Harbor (USA), 2001)).

The L-cysteine-producing bacterium can have a SAT which has been mutated to be resistant to feedback inhibition. The following mutations in SAT are known to induce resistance to feedback inhibition and are derived from *Escherichia coli*: when the methionine residue at position 256 is replaced with a glutamate residue (Japanese Patent Laid-open No. 11-155571), when the methionine residue at position 256 is replaced with an isoleucine residue (Denk, D. and Boeck, A., J. General Microbiol., 133, 515-525 (1987)), a mutation in the region from the amino acid residue at position 97 to the amino acid residue at position 273 or a deletion of the C-terminus region from the amino acid residue at position 227 (International Patent Publication WO97/15673, U.S. Pat. No. 6,218, 168), when the amino acid sequence corresponding to positions 89 to 96 of the wild-type SAT contains one or more mutations (U.S. Patent Published Application No. 20050112731(A1)), and so forth. In the cysE5 gene which encodes the mutant SAT described in the examples, the Val residue and the Asp residue at positions 95 and 96 of the wild-type SAT are replaced with an Arg residue and Pro residue, respectively.

The SAT gene is not limited to the gene of *Escherichia coli*, but can be any gene encoring a protein having the SAT activity. An SAT isozyme of *Arabidopsis thaliana* desensitized to feedback inhibition by L-cysteine is known, and the gene encoding this SAT can also be used (FEMS Microbiol. Lett., 179 (1999) 453-459). If a gene encoding a mutant SAT is introduced into a bacterium, L-cysteine-producing ability is imparted to the bacterium. To introduce a mutant SAT gene into a bacterium, various vectors which are typically used for protein expression can be used. Examples of such vectors include pUC19, pUC18, pHSG299, pHSG399, pHSG398, RSF1010, pBR322, pACYC184, pMW219 and so forth.

In order to introduce a recombinant vector containing a SAT gene into a bacterium, methods which are typically used to transform bacteria can be used, such as the method of D. A. Morrison (Methods in Enzymology, 68, 326 (1979)), treating recipient cells with calcium chloride to increase permeability of the cells for DNA (Mandel, M. and Higa, A., J. Mol. Biol., 53, 159 (1970)), and a method based on electroporation.

Furthermore, the SAT activity can also be enhanced by increasing the copy number of the SAT gene. The copy number of the SAT gene can be increased by introducing the SAT gene into a bacterium by using a vector such as those described above, or by introducing multiple copies of the SAT gene onto the chromosomal DNA of a bacterium. Multiple copies of the SAT gene are introduced by homologous recombination which targets a sequence present on the chromosomal DNA in multiple copies. A repetitive DNA or inverted repeat present at the end of a transposable element can be used as a sequence which is present on the chromosomal DNA in multiple copies. Alternatively, as disclosed in Japanese Patent Laid-open No. 2-109985, multiple copies of the SAT gene can be introduced into the chromosomal DNA by incorporating them into a transposon and transferring it.

Furthermore, it is known that the ydeD gene coding for the YdeD protein participates in secretion of metabolic products of the cysteine pathway, and L-cysteine-producing ability can also be improved by enhancing the activity of the YdeD protein (Japanese Patent Laid-open No. 2002-233384). The activity of the YdeD protein can be increased by, for example, improving expression of the ydeD gene. Expression of the ydeD gene can be improved in the same manner as that of the modification for improving expression of the dsbA gene described later. The ydeD gene of *Escherichia coli* can be obtained from *Escherichia coli* chromosomal DNA by PCR using, for example, the primers having the nucleotide sequences of SEQ ID NOS: 13 and 14.

Furthermore, by incorporating 3-phosphoglycerate dehydrogenase (PGD) desensitized to the feedback inhibition by serine, L-cysteine-producing ability can also be improved. As a gene coding for such a mutant PGD, the serA5 gene is known (described in U.S. Pat. No. 6,180,373).

Furthermore, an L-cysteine-producing *Escherichia* bacterium which has been modified to enhance expression of the cysPTWAM cluster genes coding for the sulfate/thio sulfate transport system proteins (Japanese Patent Laid-open No. 2005-137369, EP 1528108) can also be used.

Furthermore, an *Escherichia* bacterium which has L-cysteine producing-ability and has been modified to increase expression of the emrAB, emrKY, yojIH, acrEF, bcr or cusA gene (Japanese Patent Laid-open No. 2005-287333) can also be used.

Particular examples of the bacteria having L-cysteine-producing ability include, a bacterium containing a mutant SAT resistant to feedback inhibition, a bacterium having enhanced activity of the YdeD protein, and a bacterium containing a PGD protein desensitized to feedback inhibition by serine, a bacterium containing a mutant SAT resistant to feedback inhibition and having enhanced activity of the YdeD protein, a bacterium containing a mutant SAT resistant to feedback inhibition and a PGD protein desensitized to the feedback inhibition by serine, a bacterium having enhanced activity of the YdeD protein and containing a PGD protein desensitized to feedback inhibition by serine, and a bacterium containing a mutant SAT resistant to feedback inhibition and a PGD protein desensitized to feedback inhibition by serine, and having enhanced activity of the YdeD protein.

The bacterium can be obtained by modifying a bacterium belonging to the family Enterobacteriaceae which has L-cysteine-producing ability such as those described above so that the activity of the protein encoded by dsbA (henceforth also referred to as "DsbA") is increased. Alternatively, after such modification that the activity of the DsbA protein is increased is performed, L-cysteine-producing ability can be imparted. The dsbA gene is the same as ECK3852, b3860, dsf, iarA and ppfA genes.

The phrase "the activity of the protein encoded by the dsbA gene is increased" means that the activity of the DsbA protein encoded by the dsbA gene is increased as compared with a non-modified strain such as a wild-type or parent strain. The activity of the DsbA protein is essentially an activity of oxidizing a substrate protein (AmpC, DsbB, LivK, OstA, RcsF) in the periplasm, and by increasing the activity of this DsbA protein, L-cysteine-producing ability can be improved. Therefore, according to another definition, the activity of the DsbA protein means an activity of improving L-cysteine-producing ability, when the activity is increased in bacteria. Furthermore, it was revealed that when the dsbA gene was deleted, the bacterium became L-cysteine sensitive, and when the dsbA gene-deficient strain was transformed with the dsbA gene, it was recovered from the cysteine sensitivity as described in the examples. Therefore, according to another definition, the activity of the DsbA protein means a property of being involved in such cysteine resistance or sensitivity.

Such modification that the activity of the DsbA protein encoded by the dsbA gene is increased is attained by, for example, increasing expression of the dsbA gene.

Modification for enhancing expression of the dsbA gene can be attained by increasing the copy number of the dsbA gene by using, for example, a gene recombination technique. For example, a recombinant DNA can be prepared by ligating a gene fragment containing the dsbA gene with a vector functioning in a host bacterium such as a multi-copy type vector and introduced into the bacterium to transform it. Examples of the vector include vectors which are autonomously replicable in host bacterium cells. Examples of the vector autonomously replicable in *Escherichia coli* cells include pUC19, pUC18, pHSG299, pHSG399, pHSG398, pACYC184 (pHSG and pACYC series vectors are available from Takara Bio), RSF1010, pBR322, pMW219 (pMW219 is available from NIPPON GENE), pSTV29 (available from Takara Bio), and so forth.

To introduce such a recombinant DNA into a bacterium, any known transformation methods that have hitherto been reported can be employed. For instance, employable are treating recipient cells with calcium chloride so as to increase permeability thereof for DNA, which has been reported for *Escherichia coli* K-12 (Mandel, M. and Higa, A., J. Mol. Biol., 53, 159 (1970)), and preparing competent cells from cells which are at the growth phase followed by introducing the DNA thereinto, which has been reported for *Bacillus subtilis* (Duncan, C. H., Wilson, G. A. and Young, F. E., Gene, 1, 153 (1977)). In addition to these, also employable is making DNA-recipient cells into protoplasts or spheroplasts, which can easily take up recombinant DNA, followed by introducing the recombinant DNA into the cells, which is known to be applicable to *Bacillus subtilis*, actinomycetes and yeasts (Chang, S, and Choen, S. N., Mol. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci. USA, 75, 1929 (1978)).

Increase of the copy number of the dsbA gene can also be achieved by introducing multiple copies of the dsbA gene into a genomic DNA of a bacterium. In order to introduce multiple copies of the dsbA gene into a genomic DNA of a bacterium, homologous recombination is carried out by using a sequence whose multiple copies are present in the genomic DNA as targets. As sequences whose multiple copies are present in genomic DNA, repetitive DNA, and inverted repeats existing at the end of a transposable element can be used. Another dsbA gene can be introduced aside the dsbA gene existing on a genome in tandem, or it can be introduced into an unnecessary gene on a genome in a plural number. Such gene transfer can be attained by using a temperature sensitive vector or an integration vector.

Alternatively, as disclosed in Japanese Patent Laid-open No. 2-109985, it is also possible to incorporate the dsbA gene into a transposon, and allow it to transfer to introduce multiple copies of the genes into a genomic DNA. Transfer of the gene to the genome can be confirmed by performing Southern hybridization using a part of the dsbA gene as a probe.

Furthermore, in addition to the aforementioned increase of the gene copy number, expression of the dsbA gene can be enhanced by replacing an expression control sequence such as a promoter of the dsbA gene on a genome DNA or plasmid with a stronger one, by making the −35 and −10 regions of the gene closer to the consensus sequence, by amplifying a regulator that increases expression of the dsbA gene, or by deleting or attenuating a regulator that decreases expression of the dsbA gene according to the methods described in International Patent Publication WO00/18935. For example, the lac promoter, trp promoter, trc promoter, tac promoter, araBA promoter, lambda phage PR promoter and PL promoter, tet promoter, T7 promoter, Φ10 promoter, and so forth are known as strong promoters. Furthermore, the promoter of the threonine operon of *E. coli* can also be used. A promoter or SD region of the dsbA gene can also be modified so as to become stronger by introducing a nucleotide substitution or the like. Examples of methods for evaluating strength of a promoter and strong promoters are described in the paper of Goldstein et al. (Prokaryotic promoters in biotechnology, Biotechnol. Annu. Rev., 1, 105-128 (1995)) and so forth. In addition, it is known that substitution of several nucleotides in a spacer between the ribosome binding site (RBS) and translation initiation codon, especially a sequence immediately upstream from the initiation codon, greatly affects mRNA translation efficiency, and therefore this sequence can be modified. Expression control regions such as promoter of the dsbA gene can also be identified by using a promoter probe vector or gene analysis software such as GENETYX. By such substitution or modification of promoter as described above, expression of the dsbA gene is enhanced. Substitution of an expression control sequence can also be attained by, for example, a method using a temperature sensitive plasmid or Red-driven integration (WO2005/010175).

The nucleotide sequence of the dsbA gene of *Escherichia coli* and the amino acid sequence encoded by this gene are shown in SEQ ID NOS: 1 and 2, respectively. Since the nucleotide sequence of the dsbA gene can be different depending on species or strain of the bacterium, the dsbA gene to be modified can be a variant of the nucleotide sequence of SEQ ID NO: 1. Homologues of DsbA are known for many bacteria, and can be found by search of databases. When proteins highly homologous to the DsbA protein of the *E. coli* K-12 strain are searched for on the basis of sequence information, the search can be performed as, for example, BLAST search (http://www.ncbi.nlm.nih.gov/blast/Blast.cgi). Furthermore, when homologues are searched for with a keyword, if the search engine of Entrez (http://www.ncbi.nlm.nih.gov/sites/gquery) is used, and a term "dsbA" or "outer membrane channel protein" is inputted as a keyword, for example, candidate sequences are retrieved from plural databases. By scrutinizing these candidates, objective homologue sequences can be found. Among the many DsbA homologues found by such a method, nucleotide sequences of genes and amino acid sequences of DsbA homologues of the following bacteria are shown in SEQ ID NOS: 3 to 12. The accession numbers in the NCBI (National Center for Biotechnology Information) database and identity (%) with respect to the amino acid sequence of SEQ ID NO: 2 are shown in the parentheses.

*Shigella flexneri* 301 (serotype 2a) (KEGG Entry Name: SF3931, 99.5%)

*Klebsiella pneumoniae* subsp. *pneumoniae* MGH 78578 (KEGG Entry Name: KPN_04170, 81.2%)

*Yersinia enterocolitica* subsp. *enterocolitica* 8081 (KEGG Entry Name: YE0020, 70.7%)

*Photorhabdus luminescens* subsp. *laumondii* TT01 (KEGG Entry Name: p1u0381, 60.1%)

*Pasteurella multocida* PM70 (KEGG Entry Name: PM1801, 48.1%)

The dsbA gene can also encode a protein having a sequence corresponding to the amino acid sequence of the aforementioned DsbA protein or DsbA homologue, such as the amino acid sequences of SEQ ID NOS: 2, 4, 6, 8, 10 and 12, but which include substitutions, deletions, insertions, additions or the like of one or several amino acid residues at one or several positions. Although the number of the "one or several" amino acid residues can differ depending on their position in the three-dimensional structure or the types of amino acid residues of the proteins, it can be 1 to 20, 1 to 10, or even 1 to 5. These substitutions, deletions, insertions, or additions of one or several amino acid residues can be conservative mutations so that the function of the protein is maintained. A conservative mutation is a mutation wherein substitution takes place mutually among Phe, Trp and Tyr, if the substitution site is an aromatic amino acid; among Leu, Ile and Val, if the substitution site is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. Typical examples of conservative mutations are conservative substitutions. Specific examples of conservative substitutions include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val. The above-mentioned amino acid substitution, deletion, insertion, addition, inversion etc. can be a result of a naturally-occurring mutation or variation due to an individual difference or a difference of species of a microorganism as an origin of gene (mutant or variant).

Furthermore, the gene having such a conservative mutation as mentioned above can be a gene encoding a protein which has a homology of 80% or more, 90% or more, 95% or more, 97% or more, 98% or more, or even 99% or more, to the entire encoded amino acid sequence, and which has a function equivalent to that of a wild-type DsbA protein. In the present specification, the term "homology" can mean "identity".

The dsbA gene can be a DNA which hybridizes with a probe prepared from known gene sequences, for example, the aforementioned nucleotide sequence of the dsbA gene or the dsbA gene homologues, such as the sequence of SEQ ID NOS: 1, 5, 7, 9 or 11, or sequences complementary to the sequences under stringent conditions and which encodes a protein which is a functionally equivalent to the DsbA protein. The term "stringent conditions" refers to conditions where a so-called specific hybrid is formed and a non-specific hybrid is not formed. Examples thereof include conditions where DNAs having high homology, for example, at least 80%, 90%, 95%, 97%, 98%, or even 99% homology, hybridize with each other and DNAs having homology less than the value do not hybridize with each other; and specifically include conditions corresponding to a salt concentration and temperature of washing which are typical of Southern hybridization, that is, washing once or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C.

The probe can be a partial sequence of a complementary sequence of the gene. Such a probe can be prepared by PCR using oligonucleotides prepared based on the known nucleotide sequences of genes as primers, and a DNA fragment containing these sequences as the template. When a DNA fragment of a length of about 300 by is used as the probe, the conditions of washing after hybridization can be, for example, 50° C., 2×SSC, and 0.1% SDS.

The above descriptions about variants of genes and proteins are similarly applied to enzymes such as serine acetyltransferase and cysteine desulfhydrase, the YdeD protein, and the genes that code for them.

<2> Method for Producing L-cysteine, L-cystine, Derivatives or Precursors Thereof or Mixture Thereof These compounds can be produced by culturing the bacterium obtained as described above in a medium, and collecting L-cysteine, L-cystine, derivatives or precursors thereof or a mixture thereof from the medium. Examples of a derivative or precursor of L-cysteine include S-sulfocysteine, a thiazolidine derivative, a hemithioketal corresponding the thiazolidine derivative mentioned above, O-acetylserine, N-acetylserine, and so forth.

Examples of the medium used for the culture can include ordinary media containing a carbon source, nitrogen source, sulfur source, inorganic ions, and other organic components as required.

As the carbon source, saccharides such as glucose, fructose, sucrose, molasses and starch hydrolysate, and organic acids such as fumaric acid, citric acid and succinic acid can be used.

As the nitrogen source, inorganic ammonium salts such as ammonium sulfate, ammonium chloride and ammonium phosphate, organic nitrogen such as soybean hydrolysate, ammonia gas, aqueous ammonia and so forth can be used.

As the sulfur source, inorganic sulfur compounds, such as sulfates, sulfites, sulfides, hyposulfites and thiosulfates can be used.

As organic trace amount nutrients, it is desirable to add required substances such as vitamin $B_1$, yeast extract and so forth in appropriate amounts. Other than these, potassium phosphate, magnesium sulfate, iron ions, manganese ions and so forth are added in small amounts.

The culture can be performed under aerobic conditions for 30 to 90 hours. The culture temperature can be controlled to be 25° C. to 37° C., and the pH can be controlled to be 5 to 8 during the culture. To adjust the pH, inorganic or organic acidic or alkaline substances, ammonia gas and so forth can be used. Collection of L-cysteine from the culture can be attained by, for example, any combination of known ion exchange resin methods, precipitation, and other known methods.

L-cysteine obtained as described above can be used to produce L-cysteine derivatives. The cysteine derivatives include methylcysteine, ethylcysteine, carbocysteine, sulfocysteine, acetylcysteine, and so forth.

Furthermore, when a thiazolidine derivative of L-cysteine is produced in the medium, L-cysteine can be produced by collecting the thiazolidine derivative from the medium to break the reaction equilibrium between the thiazolidine derivative and L-cysteine so that L-cysteine is excessively produced. Furthermore, when S-sulfocysteine is produced in the medium, it can be converted into L-cysteine by reduction with a reducing agent such as dithiothreitol.

EXAMPLES

Hereinafter, the present invention will be explained more specifically with reference to the following non-limiting examples. In the following descriptions, cysteine means L-cysteine.

(1) Screening of Clones Showing Cysteine Sensitivity

In order to comprehensively search for genes participating in cysteine resistance, the Keio collection (single gene-knock out library except for essential genes of E. coli BW25113, Baba, T, et al., 2006, Mol. Syst. Biol., 2:2006.0008) was screened for clones showing sensitivity to cysteine.

(1-1) Screening of Keio Collection for Clones Showing Cysteine Sensitivity

The 3,985 clones of the Keio collection were cultured at 37° C. for 15 hours in 0.5 ml of LB liquid medium. This culture medium was stamped on LB agar media containing cysteine at different concentrations (0, 15, 20, 25 mM), and culture was performed overnight at 37° C. Clones that were cysteine sensitive at the growth inhibition concentration of cysteine for wild-type strains (20 mM) were visually selected. Specifically, clones that did not form colonies on the LB plate containing 15 mM cysteine were selected as candidates. A dsbA gene-deficient strain was obtained as a clone showing particularly strong and distinctive cysteine sensitivity among the above candidates.

DsbA localizes in the periplasm, and forms disulfide bond (S—S bond) in a substrate protein by utilizing the oxidized state (—S—S—) and the reduced state (—SH/—SH) of two cysteine residues of DsbA itself to induce folding of the substrate protein. At the time of the S—S bond formation of the substrate protein, the cysteine residues of DsbA changes from those of the oxidized type (—S—S—) into the reduced type (—SH/—SH). As a protein that recycles the reduced type DsbA produced as described above into the oxidized type, DsbB is known. It was elucidated that the electrons received by DsbB are transferred to ubiquinone (UQ), which is a respiratory chain component, and oxygen finally serves as an electron acceptor with the aid of cytochrome oxidase. Therefore, a series of these DsbA, DsbB, and the respiratory chain system play a role of performing the oxidative crosslinking reaction of cysteine residues on a substrate protein. Although it was known that the cysteine residues in a protein were used as a substrate as described above, it was unpredictable that the addition of a low molecule cysteine itself had a certain influence on that system.

(1-2) Cysteine Sensitivity Induced by dsbA Gene Deficiency

Since a dsbA-deficient strain was obtained by the screening of the Keio Collection, growth of the gene-deficient strain was observed on the agar medium containing cysteine of different concentrations in order to analyze the sensitivity of that strain to cysteine in more detail. Furthermore, as for the to/C gene (Japanese Patent Application No. 2008-040167, Wiriyathanawudhiwong, N. et al., Appl. Microbiol. Biotechnol. (2009) 81:903-913), which was previously obtained in a similar manner, and of which deletion is known to induce cysteine sensitivity, a similar experiment was performed by using a to/C-deficient strain. The dsbA-deficient strain and to/C-deficient strain used in this experiment were JW3832 strain and JW5503 strain, respectively (both were included in the Keio collection), and their parent strain was the BW25113 strain (Andreas Haldimann, A. and Wanner, B. L., J. Bacteriol., 2001 November, 183 (21):6384-6393). The plasmids carrying the dsbA gene and the to/C gene for the complementation experiment were pDsbA and pTo1C (ASKA clone (Kitagawa, M., et al., 2005, DNA Res., 12:291-299)), and the vector used as the base of them was pCA24 (vector for ASKA clone (Kitagawa, M., et al., 2005, DNA Res., 12:291-299)).

The bacteria containing each of the plasmids were each inoculated into 5 ml of L medium (10 g/L of Bacto trypton, 5 g/L of Bacto yeast extract, 5 g/L of NaCl), and cultured overnight at 30° C. The culture was serially diluted 10 times for every dilution with 0.9% physiological saline to prepare serially diluted cell suspensions ($10^{-2}$ to $10^{-6}$), and the cell suspensions were spotted (5 µl) onto L agar medium (10 g/L of Bacto trypton, 5 g/L of Bacto yeast extract, 5 g/L of NaCl, 15 g/L of agar) containing various concentrations (10, 15, 20 mM) of cysteine. Culture was performed at 37° C. overnight, and growth tests of the dsbA-deficient strain and the to/C-deficient strain in the cysteine medium, and complementation (recovery of growth) tests with the dsbA plasmid and the to/C plasmid were performed. The results are shown in FIG. 1. The dsbA-deficient strain JW3832/pCA24 and the to/C-deficient strain JW5503/pCA24 showed marked cysteine sensitivity as compared with the control strain BW25113/pCA24, and when the dsbA and to/C gene were introduced as plasmids (JW3832/pDsbA strain, JW5503/pTolC strain), the strains recovered from the sensitivity. Therefore, it was found that DsbA was involved in the cysteine resistance, like to/C.

(2) Toxicity of Cysteine to Cell and Relation to DsbA

Since deficiency of the dsbA gene induced cysteine sensitivity, experiments were performed about toxicity of cysteine to cells and relation thereof to DsbA.

(2-1) Accumulation of Reduced Type DsbA Induced by Cysteine

In order to examine whether cysteine has any influence on the oxidized and reduced states of the DsbA protein, the oxidized and reduced states of DsbA were analyzed when cysteine was added, or YdeD, a cysteine secretion factor, was highly expressed. It is known that YdeD is a secretion protein localizing at cell membranes, and participates in transportation from cytoplasm to periplasm (Dasler, T. et al., Mol. Microbiol., 2000, 36:1101-1112). Therefore, it is estimated that if YdeD is highly expressed, the supply of cysteine to the periplasm is increased.

The strains used in this experiment were the E. coli BW25113 strain (Andreas Haldimann and Barry L. Wanner, J. Bacteriol., 2001 November, 183 (21):6384-6393) as a wild-type parent strain, the dsbA-deficient JW3832 strain and dsbB-deficient JW5182 strain derived from BW25113 strain (Baba, T, et al., 2006, Mol. Syst. Biol., 2:2006.0008). As a plasmid carrying the dsbB gene, pDsbB (ASKA clone, Kitagawa, M. et al., 2005, DNA Res., 12:291-9) was used.

A plasmid pYdeD carrying the ydeD gene for highly expressing YdeD was constructed as follows. PCR was performed by using the genomic DNA of the E. coli MG1655 strain as a template, P1 (5'-CGCGGATCCAATGGTCAT-AAATGGCAGCGTAGCGC-3': SEQ ID NO: 13) and P2 (5'-CGCGGATCCGCAGGGCGTTGCGGAACAAAC-3': SEQ ID NO: 14) as primers according to the protocol attached to Pyrobest DNA polymerase (Takara) to obtain a ydeD gene fragment of about 1.5 kb including a region of about 300 by upstream from the ydeD gene and a region of about 200 by downstream from the ydeD gene. The BamHI site was designed in both the primers. The PCR fragment was digested with BamHI, and then inserted into pSTV29 (Takara) at the BamHI site, and the obtained plasmid in which the ydeD gene fragment was inserted in the same direction as the lacZ gene on the pSTV29 vector was designated plasmid pYdeD. The amplified portion was sequenced by PCR to confirm that it did not contain a mutation.

In order to distinguish the oxidized state and the reduced state of the DsbA protein, the protein was modified with AMS (4-acetamido-4'-maleimidyl-stilbene-2,2'-disulfonate) (Kadokura, H. et al., 2004, Science, 303, 534-537). Each of the wild-type strain, the dsbA-deficient strain, the dsbB-deficient strain, the wild-type strain +pYdeD and the dsbB-deficient strain +pDsbB was cultured overnight at 30° C. in 3 ml of LB medium, and the resulting culture was used as a preculture medium. The preculture medium was inoculated into the LB medium in a 1% amount, and culture was performed at 30° C. with shaking until $OD_{660}$ reached 0.4 to 0.5. Then, cysteine was added at 5 mM as the final concentration to expose the cells to cysteine for 20 minutes. The oxidized and reduced states of the DsbA protein were examined by the method of Ito et al. (Kobayashi, T., Kishigami, S., Sone, M., Inokuchi, H., Mogi, T. and Ito K., Proc. Natl. Acad. Sci. USA, 94, 11857-11862). That is, after giving the stress, 100 μl of TCA (trichloroacetic acid, final concentration: 16.7%) was immediately added to 0.5 ml of the culture medium ($OD_{660}$ was about 0.5), and the mixture was stirred, left standing on ice for 20 minutes to precipitate the cells, and centrifuged to collect the cells. Then, 700 μl of acetone was added to the obtained precipitates, the mixture was stirred, then left standing on ice for 20 minutes, and recentrifuged to collect the cells. The precipitates were dissolved in a solution of 1% SDS, 50 mM Tris-HCl (pH 6.8) and 10 mM 4-acetamido-4'-maleimidyl-stilbene-2,2'-disulfonate (AMS, Invitrogen) prepared immediately before use.

The labeled protein was then separated by non-reduced SDS gel electrophoresis (12.5%), and then detected by Western blotting. The nitrocellulose membrane after the blotting was shaken in a blocking solution (TTBS containing 3% of skim milk, 0.05% (wt/vol) of Tween 20, 200 mM Tris-HCl (pH 7.5), 500 mM NaCl) for 1 hour. The membrane was washed with TTBS, and then shaken in a primary antibody solution (anti-DsbA blood serum (rabbit), Kadokura, H. et al., 2004, Science, 303, 534-537) for 1 hour. The membrane was washed with TTBS, and then shaken in a secondary antibody solution (TTBS containing 0.2% of peroxidase-labeled anti-rabbit IgG (GE Healthcare) and 3% of albumin). The label was detected by using ECL Plus Western Blotting Detection Reagents (Amersham).

Figure 2:
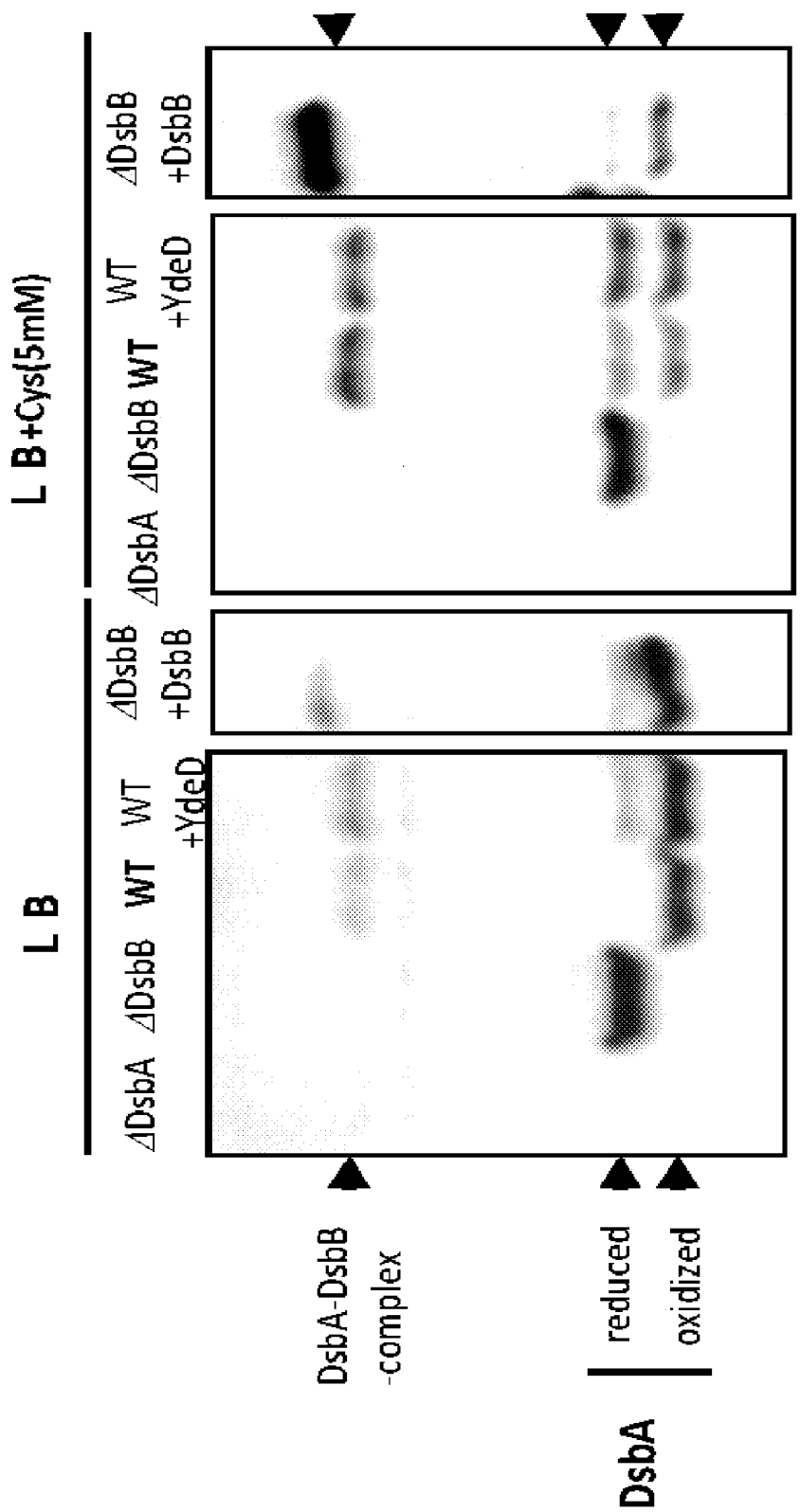
FIG. 2 shows oxidized and reduced states of the DsbA protein provided by cysteine (electrophoresis photograph).

The results are shown in FIG. 2. From the fact that no band was detected for the dsbA-deficient strain, and the appearance of the bands for the dsbB-deficient strain and dsbB-deficient strain +pDsbB, it was confirmed that the oxidized type and reduced type of DsbA were correctly detected. When cysteine was not added, only the oxidized type DsbA was observed for the wild-type strain. However, the reduced type DsbA accumulated after exposure to cysteine (reduction stress), and the DsbA-DsbB complex also markedly accumulated. Moreover, it was found that the reduced type DsbA also accumulated in the wild-type strain when YdeD was highly expressed in that strain. The DsbA-DsbB-UQ oxidation system is originally a system for disulfide bond formation in proteins. However, it was found that when cysteine excessively existed, it worked to oxidize it into cystine, and thus the reduced type DsbA accumulated.

(2-2) Accumulation of Reduced Type OstA Protein Induced by Cysteine

Since it was elucidated that the reduced type DsbA was accumulated by cysteine (reduction stress), it was decided to investigate toxicity of cysteine and oxidized and reduced states of a protein in the periplasm. The OstA is a protein in the periplasm indispensable to growth, and requires disulfide bond formed by DsbA. In order to investigate the oxidized and reduced states of the OstA protein, the E. coli BW25113 strain as the wild-type parent strain and the dsbA-deficient JW3832 strain derived from the BW25113 strain were used, and the plasmid pmyc-OstA for expressing OstA fused with an Myc tag (Kadokura, H. et al., 2004, Science, 303, 534-537) was introduced into them. Under the same culture conditions as those of the aforementioned experiment for investigating the oxidized and reduced states of DsbA, addition of L-cysteine (final concentration: 5 mM) and modification of the protein with AMS (4-acetamido-4'-maleimidyl-stilbene-2,2'-disulfonate) were performed, and the OstA protein was detected by Western blotting. As the antibody, anti-Myc (mouse) was used in this experiment.

Figure 3:
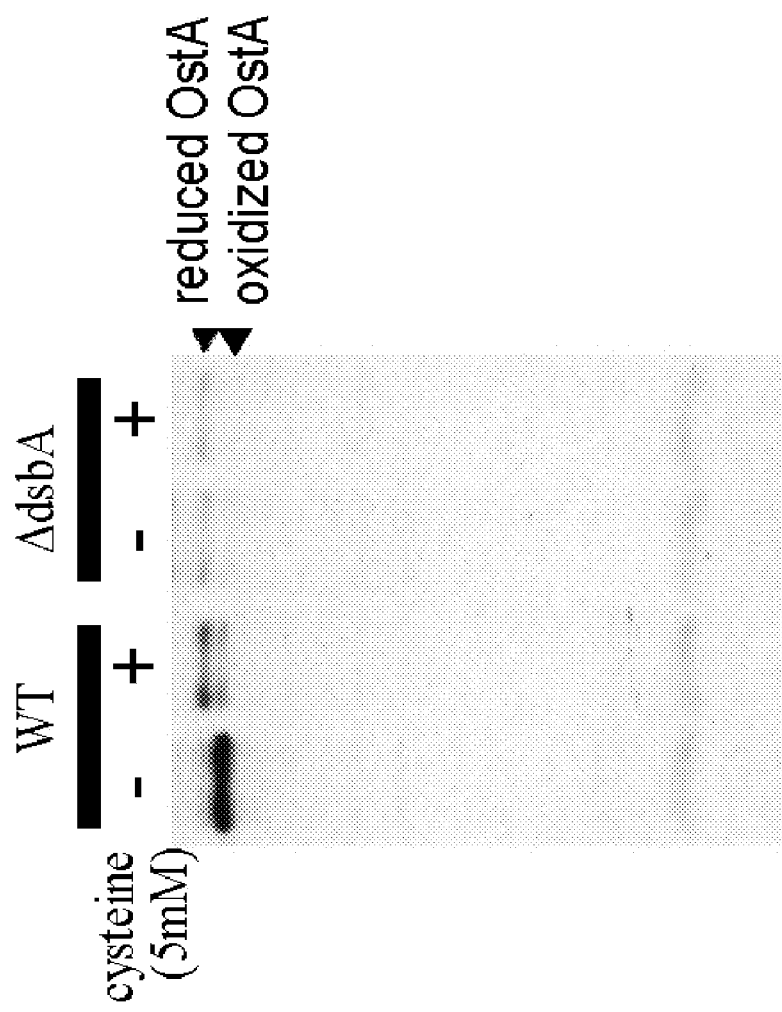
FIG. 3 shows oxidized and reduced states of the OstA protein provided by cysteine (electrophoresis photograph).

The results are shown in FIG. 3. It was found that, in the DsbA-deficient strain, all of the OstA proteins are the reduced type, irrespective of addition or no addition of cysteine. In the wild-type strain, when there was no cysteine, the OstA protein was the oxidized type with correctly formed disulfide bond, but the reduced type accumulated after the addition of cysteine. It was elucidated that the reduced type DsbA accumulated due to cysteine (reduction stress), accordingly the OstA protein which is as an essential protein was not correctly oxidized, and this constituted one of toxicities of cysteine for growth. On the basis of the above consideration, it was considered that enhancement of DsbA was effective in an environment where cysteine abundantly existed such as that of cysteine production by fermentation.

(3) Construction of Cysteine-producing Bacterium

A cysteine-producing bacterium was constructed by introducing pACYC-DES carrying a mutant cysE coding for a mutant serine acetyltransferase in which feedback inhibition by L-cysteine was reduced, the ydeD gene, and a mutant serA gene coding for a 3-phosphoglycerate dehydrogenase in which feedback inhibition by L-serine was reduced on one plasmid into E. coli BW25113. The construction of pACYC-DES is described in EP 1528108 B1. Furthermore, in order to investigate the effect of overexpression of DsbA on cysteine production, cysteine-producing bacteria introduced with pDsbA or an empty vector pCA24N serving as a control were constructed.

E. coli BW25113 can be obtained from the Escherichia coli Genetic Stock Center (830 Kline Biology Tower, Dept. of Molecular, Cellular, and Developmental Biology, 266 Whitney Ave., PO box 208103, Yale University, New Haven, Conn. 06520-8103) by referring to the number of CGSC#7636. An L-cysteine-producing bacterium can also be similarly constructed by using the E. coli W3110 strain or the like instead of the above strain. E. coli K12 W3110 can be obtained from ATCC as ATCC 27325.

(4) L-Cysteine Production by DsbA-Enhanced Cysteine-Producing Bacterium

A DsbA-enhanced cysteine-producing bacterium (E. coli BW25113/pACYC-DES/pDsbA strain), and a DsbA-non-enhanced control strain (E. coli BW25113/pACYC-DES/pCA24N strain) were each inoculated into 5 ml of L medium (10 g/L of Bacto trypton, 5 g/L of Bacto yeast extract, 5 g/L of NaCl, tetracycline (10 μg/mL), chloramphenicol (30 μg/mL)), and cultured at 30° C. overnight (preculture).

The cell suspension after an overnight culture was taken in a volume of 250 μl, and added to 25 ml of the fresh medium (SM1+10% L medium), and culture was performed at 30° C. with shaking at 140 rpm. In this culture, tetracycline (10 mg/mL) and chloramphenicol (30 μg/mL) were added to the medium in order to maintain the plasmids in the cells. The medium was temporally sampled, and production of cysteine, cystine, and cysteine-related compounds were analyzed after various periods. The composition of the SM1 medium used for the culture was as follows: 0.1 M $KH_2PO_4$—$K_2HPO_4$ buffer (pH 7.0), 30 g/L of glucose, 10 g/L of $(NH_4)_2SO_4$, 0.1 g/L of NaCl, 7.2 μM $FeSO_4.7H_2O$, 0.6 μM $Na_2MoO_4$, 40.4 μM $H_3BO_3$, 2.9 μM $CoCl_2$, 1 μMl $CuSO_4$, 8.1 μM $MnCl_2$, 1 mM $MgSO_4$, 0.1 mM $CaCl_2$ (Dassler, T. et al., 2000, Mol. Microbiol., 36, 1101-1112).

Figure 4:
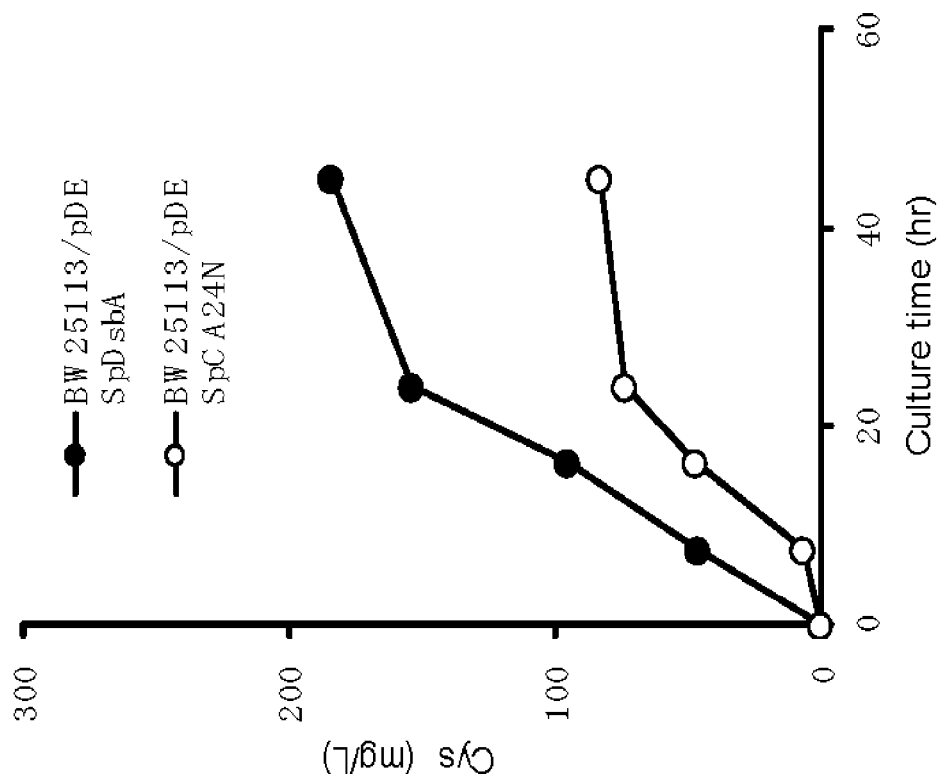
FIG. 4 shows cysteine production by a DsbA-enhanced cysteine-producing bacterium.

Cysteine, cystine, and cysteine-related compounds were quantified as follows according to the method of Gaitonde (Gaitonde, M. K., 1967, Biochem. J., 104, 627-633). The Gaitonde reagent (250 mg of ninhydrin, 6 ml of acetic acid, 4 ml of hydrochloric acid) in a volume of 200 μl was added to 100 μl of the culture medium, the coloration reaction was performed at 100° C. for 5 minutes, 400 μl of 100% ethanol was added to the mixture, and $OD_{560}$ of the mixture was measured. Change of the amounts of cysteine accumulated in the medium (amounts quantified by the Gaitonde method) is shown in FIG. 4. In the Figure, "Cys" represents the total amount including the amounts of cystine and cysteine-related compounds. Furthermore, BW25113/pDESpDsbA and BW25113/pDESpCA24N represent BW25113/pACYC-DES/pDsbA and BW25113/pACYC-DES/pCA24N, respectively. It was found that the amount of cysteine markedly increased in the DsbA-enhanced strain. Thus, it became clear that enhancement of DsbA had an effect of increasing cysteine production amount.

(5) Cysteine Production by DsbB, DsbC, DsbD and DsbG-Enhanced Cysteine-producing Bacterium Since DsbB promotes re-oxidation of DsbA, enhancement thereof can be expected to have the same effect as that of DsbA enhancement. Furthermore, a similar effect can be expected for enhancement of DsbC-DsbD or DsbG similar to the system of DsbA-DsbB. Enhancement of DsbB, DsbC, DsbD and DsbG in a cysteine-producing bacterium can be attained by, for example, introducing the ASKA clone plasmids of each gene into *E. coli* BW25113/pACYC-DES strain, as performed for obtaining the DsbA-enhanced strain. By culturing and analyzing each cysteine-producing bacterium prepared as described above in the same manners as those used in the experiments for DsbA-enhanced strain, it can be demonstrated that each gene has an effect of improving cysteine production.

EXPLANATION OF SEQUENCE LISTING

SEQ ID NO: 1: Nucleotide sequence of *E. coli* dsbA gene
SEQ ID NO: 2: Amino acid sequence of *E. coli* DsbA
SEQ ID NO: 3: Nucleotide sequence of *Shigella flexneri* dsbA gene homologue
SEQ ID NO: 4: Amino acid sequence of *Shigella flexneri* DsbA homologue
SEQ ID NO: 5: Nucleotide sequence of *Klebsiella pneumoniae* dsbA gene homologue
SEQ ID NO: 6: Amino acid sequence of *Klebsiella pneumoniae* DsbA homologue
SEQ ID NO: 7: Nucleotide sequence of *Yersinia enterocolitica* dsbA gene homologue
SEQ ID NO: 8: Amino acid sequence of *Yersinia enterocolitica* DsbA homologue
SEQ ID NO: 9: Nucleotide sequence of *Photorhabdus luminescens* dsbA gene homologue
SEQ ID NO: 10: Amino acid sequence of *Photorhabdus luminescens* DsbA homologue
SEQ ID NO: 11: Nucleotide sequence of *Pasteurella multocida* dsbA gene homologue
SEQ ID NO: 12: Amino acid sequence of *Pasteurella multocida* DsbA homologue
SEQ ID NO: 13: Primer P1 for ydeD gene amplification
SEQ ID NO: 14: Primer P2 for ydeD gene amplification While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing a compound selected from the group consisting of L-cysteine, L-cystine, and a derivative or precursor thereof, which comprises culturing a bacterium belonging to the family *Enterobacteriaceae* in a medium and collecting the compound from the medium,
   wherein the bacterium is able to produce L-cysteine and has been modified to increase the activity of a protein encoded by the dsbA gene as compared to a non-modified bacterium,
   wherein the activity of the protein is increased by a method selected from the group consisting of:
   i) increasing expression of the dsbA gene by increasing the copy number of the dsbA gene or by modifying an expression control sequence of the dsbA gene,
   ii) increasing translation of the dsbA gene, and
   iii) combinations thereof,
   wherein the protein is selected from the group consisting of:
   (A) a protein comprising the amino acid sequence of SEQ ID NO: 2, 4, 6, 8, 10 or 12, and
   (B) a protein comprising the amino acid sequence of SEQ ID NO: 2, 4, 6, 8, 10 or 12, but which includes substitutions, deletions, insertions or additions of one to 5 amino acid residues, and wherein the increase of the protein's activity in the bacterium improves the ability of the bacterium to produce L-cysteine.

2. The method according to claim 1, wherein the derivative of L-cysteine is a thiazolidine derivative.

3. The method according to claim 1, wherein the precursor of L-cysteine is O-acetylserine or N-acetylserine.

4. The method according to claim 1 wherein the dsbA gene is selected from the group consisting of:
   (a) a DNA comprising the nucleotide sequence of SEQ ID NO: 1, 3, 5, 7, 9 or 11, and
   (b) a DNA which hybridizes with a sequence complementary to the nucleotide sequence of SEQ ID NO: 1, 3, 5, 7, 9 or 11 under stringent conditions comprising washing at a salt concentration and temperature corresponding to 0.1×SSC, 0.1% SDS at 60° C., and codes for a protein wherein the increase of the protein's activity in the bacterium improves the ability of the bacterium to produce L-cysteine.

5. The method according to claim 1, wherein the bacterium contains a serine acetyltransferase which has been mutated to attenuate feedback inhibition by L-cysteine.

6. The method according to claim 1, wherein the bacterium has been modified so that the activity of the protein encoded by the ydeD gene is increased.

7. The method according to claim 1, wherein 3-phosphoglycerate dehydrogenase has been desensitized to feedback inhibition by serine.

8. The method according to claim 5, wherein the bacterium has been modified so that the activity of the protein encoded by the ydeD gene is increased.

9. The method according to claim 7, wherein the bacterium has been modified so that the activity of the protein encoded by the ydeD gene is increased.

10. The method according to claim 1, wherein the bacterium is an *Escherichia* bacterium.

11. The method according to claim 10, wherein the bacterium is *Escherichia coli*.

* * * * *